US010918715B2

(12) United States Patent
Langohr et al.

(10) Patent No.: US 10,918,715 B2
(45) Date of Patent: Feb. 16, 2021

(54) TREATMENT OF SEVERE COMMUNITY ACQUIRED PNEUMONIA

(71) Applicant: BIOTEST AG, Dreieich (DE)

(72) Inventors: Patrick Langohr, Hattersheim (DE); Andrea Wartenberg-Demand, Schrecksbach (DE); Ulrike Wippermann, Dreieich (DE); Benjamin Daelken, Frankfurt (DE)

(73) Assignee: BIOTEST AG, Dreieich (DE)

( * ) Notice: Subject to any disclaimer, the term of this patent is extended or adjusted under 35 U.S.C. 154(b) by 0 days.

(21) Appl. No.: 16/786,639

(22) Filed: Feb. 10, 2020

(65) Prior Publication Data

US 2020/0268881 A1 Aug. 27, 2020

Related U.S. Application Data

(63) Continuation of application No. 16/085,234, filed as application No. PCT/EP2017/055838 on Mar. 13, 2017.

(30) Foreign Application Priority Data

Mar. 14, 2016 (EP) .................................. 16160175
Aug. 22, 2016 (EP) .................................. 16185173

(51) Int. Cl.
| | |
|---|---|
| *A61K 39/395* | (2006.01) |
| *A61K 9/00* | (2006.01) |
| *C07K 16/06* | (2006.01) |
| *G01N 33/68* | (2006.01) |
| *C07K 16/00* | (2006.01) |
| *G01N 33/74* | (2006.01) |
| *A61K 39/00* | (2006.01) |
| *A61K 35/16* | (2015.01) |

(52) U.S. Cl.
CPC .......... *A61K 39/395* (2013.01); *A61K 9/0019* (2013.01); *C07K 16/00* (2013.01); *C07K 16/065* (2013.01); *G01N 33/6854* (2013.01); *G01N 33/6893* (2013.01); *G01N 33/74* (2013.01); *A61K 35/16* (2013.01); *A61K 2039/507* (2013.01); *G01N 2333/4737* (2013.01); *G01N 2333/585* (2013.01); *G01N 2800/12* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,318,902 A | 3/1982 | Stephan |
| 5,190,752 A | 3/1993 | Moller |
| 7,794,721 B2 | 9/2010 | Simon |

FOREIGN PATENT DOCUMENTS

| | | |
|---|---|---|
| EP | 0013901 A1 | 8/1980 |
| EP | 0352500 A2 | 1/1990 |
| RU | 2470664 C2 | 12/2012 |
| RU | 2012149743 A | 5/2014 |
| RU | 2536937 C2 | 12/2014 |
| WO | WO2010045193 | 4/2010 |
| WO | WO2011131786 | 10/2011 |
| WO | WO2011131787 | 10/2011 |
| WO | WO2013132052 | 9/2013 |

OTHER PUBLICATIONS

European Pharmacopoeia Version 7.0, Chapter 2.2.1, Published Jul. 2010 (Implementation date: Jan 2011), pp. 21-22.
European Pharmacopoeia Version 7.0, Chapter 2.7.1, Published Jul. 2010 (Implementation date: Jan. 2011), pp. 201-202.
European Pharmacopoeia Version 8.7, Chapter 2.6.15, Published Oct. 2015 (Implementation date: Apr. 2016), p. 5475.
European Pharmacopoeia Version 8.0, Chapter 2.6.17, Published Jul. 2013 (Implementation date: Jan. 2014), pp. 200-202.
European Pharmacopoeia Version 10.0, Text Jan. 2012:0918, Human Normal Immunoglobulin for Intravenous Administration, Published Jul. 2019 (Implementation date: Jan. 1, 2020), pp. 2862-2863.
Translation of Russian Search Report for Application No. RU 2018135290, dated Apr. 15, 2020.
Translation of Russian Official Action for Application No. RU 2018135290, dated Apr. 15, 2020.
Anonymous: "News: Biotest AG: Biotest's IgM Concentrate shows encouraging results in life-threatening pneumonia" Jun. 30, 2015 (Jun. 30, 2015), XP055286903, Retrieved from the Internet: URL:http://www.biotest.com/de/en/investorrelations/news and publications/biotest press releases/press-detail.cfm?instance TD=2768&cmfaction=xmldetail.xmldetail.detailview&showdetails=WCSWYBVZMRGXRZIVGNOCLTGA [retrieved on Jul. 8, 2016].
Becze Zsolt et al: "Can procalcitonin levels indicate the need for adjunctive therapies in sepsis?", International Journal of Antimicrobial Agents, vol. 46, 2015, XP029344395, ISSN: 0924-8579, DOI: 10.1016/J.IJANTIMICAG.2015.11.002.
Luis M Coelho et al: "Patterns of c-reactive protein RATIO response in severe community-acquired pneumonia: a cohort study" Critical Care, Biomed Central Ltd., London, GB, vol. 16, No. 2, Mar. 26, 2012 (Mar. 26, 2012), p. R53, XP021126004, ISSN: 1364-8535, DOI: 10.1186/CC11291.
Pedro P. Espana et al: "Performance of pro-adrenomedullin for identifying adverse outcomes in community-acquired pneumonia" Journal of Infection., vol. 70, No. 5, May 1, 2015 (May 1, 2015), pp. 457-466, XP055286906, GB ISSN: 0163-4453, DOI: 10.1016/j.jinf.2014.12.003.
Pereira Jose Manuel et al: "Can we predict pneumococcal bacteremia in patients with severe community-acquired pneumonia?" Journal of Critical Care, vol. 28, No. 6, 2013, pp. 970-974, XP028769594, ISSN: 0883-9441, DOI: 10.1016/J.JCRC.2013.04.016.

(Continued)

*Primary Examiner* — Brian Gangle
(74) *Attorney, Agent, or Firm* — Meunier Carlin & Curfman LLC

(57) ABSTRACT

The present invention provides for a new therapeutic tools capable of treating infectious diseases, in particular, a new pharmaceutical composition comprising an IgM-enriched immunoglobulin preparation for use in the adjunctive treatment of severe Community Acquired Pneumonia (sCAP).

23 Claims, 11 Drawing Sheets

(56) References Cited

OTHER PUBLICATIONS

R. P. Dellinger et al: "Surviving Sepsis Campaign: International Guidelines for Management of Severe Sepsis and Septic Shock, 2012", Intensive Care Medicine, vol. 39, No. 2, Feb. 1, 2013 (Feb. 1, 2013), pp. 165-228, XP055286924, DE ISSN: 0342-4642, DOI: 10.1007/s00134-012-2769-8.
Welte Tobias et al Concept for a study 1,3-9, design in patients with severe 11-26 community-acquired pneumonia: a randomized controlled trial with a novel! GM-enriched immunoglobulin preparation— The CIGMA Respiratory Medicine, vol. 109, No. 6, Apr. 2, 2015 (Apr. 2, 2015) • pp. 758-767, XP029244153, ISSN: 0954-6111, DOI: 10.1016/J.RMED.2015.03.008 abstract p. 760, right-hand column, paragraph 5-paragraph 6 p. 761.
International Search Report and Written Opinion issued in related International PCT Application No. PCT/EP2017/055838 dated Jun. 12, 2017.
Bermejo-Martín, J. F., et al. "Immunoglobulins IgG1, IgM and IgA: a synergistic team influencing survival in sepsis." Journal of internal medicine 276.4 (2014): 404-412.
Cillóniz, Catia, et al. "Microbial aetiology of community-acquired pneumonia and its relation to severity." Thorax 66.4 (2011): 340-346.
Mari, C. de la Tone, et al. "Serum immunoglobulins in the infected and convalescent phases in community-acquired pneumonia." Respiratory medicine 107.12 (2013): 2038-2045.
Dellinger, R. Phillip, et al. "Surviving Sepsis Campaign Guidelines Committee including the Pediatric Subgroup Surviving sepsis campaign: international guidelines for management of severe sepsis and septic shock: 2012." Crit Care Med 41.2 (2013): 580-637.
Geier, C., et al. "Influence of the serum levels of immunoglobulins on clinical outcomes in medical intensive-care patients." Medizinische Klinik-Intensivmedizin und Notfallmedizin 112.1 (2017): 30-37.
Giamarellos-Bourboulis, Evangelos J., et al. "Kinetics of circulating immunoglobulin M in sepsis: relationship with final outcome." Critical Care 17.5 (2013):R247.
Jensen, Jens Ulrik, et al. "Procalcitonin increase in early identification of critically ill patients at high risk of mortality." Critical care medicine 34.10 (2006): 2596-2602.
Johansson, Niclas, et al. "Procalcitonin levels in community-acquired pneumonia-correlation with aetiology and severity." Scandinavian journal of infectious diseases 46.11 (2014): 787-791.
Justel, Mar, et al. "IgM levels in plasma predict outcome in severe pandemic influenza." Journal of Clinical Virology 58.3 (2013): 564-567.
Knaus, William A., et al. "APACHE II: a severity of disease classification system." Critical care medicine 13.10 (1985): 818-829.
Kreymann, Georg K., et al. "Use of polyclonal immunoglobulins as adjunctive therapy for sepsis or septic shock." Critical care medicine 35.12 (2007): 2677-2685.
Mandell, Lionel A., et al. "Infectious Diseases Society of America/American Thoracic Society consensus guidelines on the management of community-acquired pneumonia in adults." Clinical infectious diseases 44.Supplement_2 (2007): S27-S72.
Mandell, Lionel A., et al. "Update of practice guidelines for the management of community-acquired pneumonia in immunocompetent adults." Clinical Infectious Diseases 37.11 (2003): 1405-1433.
Niederman, Michael S., et al. "Guidelines for the management of adults with community-acquired pneumonia: diagnosis, assessment of severity, antimicrobial therapy, and prevention." American journal of respiratory and critical care medicine 163.7 (2001): 1730-1754.
Que, Y-A., et al. "Assessment of panobacumab as adjunctive immunotherapy for the treatment of nosocomial Pseudomonas aeruginosa pneumonia." European journal of clinical microbiology & infectious diseases 33.10 (2014): 1861-1867.
Reinhart et al., "Prevention, diagnosis, therapy and follow-up care of sepsis: 1st revision of S-2k guidelines of the German Sepsis Society (Deutsche Sepsis-Gesellschaft e.V. (DSG)) and the German Interdisciplinary Association of Intensive Care and Emergency Medicine (Deutsche Interdisziplináre Vereinigung fúr Intensiv- and Notfallmedizin (DIVI))", GMS German Medical Science (2010) vol. 8:Doc14, ISSN 1612-3174, 86 pages.
Schoenfeld, David A., and Gordon R. Bernard. "Statistical evaluation of ventilator-free days as an efficacy measure in clinical trials of treatments for acute respiratory distress syndrome." Critical care medicine 30.8 (2002): 1772-1777.
Schmiedl et al., 2011, "Pharmacokinetics and tolerability of the IgM-enriched Immunoglobulin concentrate BT086 in healthy Subjects after single dose with dose escalation", English Language translation included.
Schmiedl et al., 2011, "Pharmacokinetics and tolerability of the IgM-enriched Immunoglobulin concentrate BT086 in healthy subjects after multiple doses", English Language translation included.
Shankar-Hari, Manu, et al. "Endogenous IgG hypogammaglobulinaemia in critically ill adults with sepsis: systematic review and meta-analysis." Intensive care medicine 41.8 (2015): 1393-1401.
Venet, Fabienne, et al. "Assessment of plasmatic immunoglobulin G, A and M levels in septic shock patients." International immunopharmacology 11.12 (2011): 2086-2090.
Werdan, Immunoglobulin treatment in sepsis—Is the answer 'no'? Crit. Care Med. (2006) vol. 34, No. 5, pp. 1542-1543.
Werdan, "The long and short of sedation practices: Daily interruption or bolus dosing?" Crit. Care Med. (2006) vol. 34, No. 5, pp. 1544.
Werdan, "Expert Interview on Sepsis Therapy with Immunoglobulins", Intensive-News Germany, (2012) Issue 4/12, 2 pages.

TREATMENT OF SEVERE COMMUNITY ACQUIRED PNEUMONIA

This application is a continuation of and claims priority to U.S. application Ser. No. 16/085,234, filed on Sep. 14, 2018, which is a national stage application filed under 35 U.S.C. § 371 of PCT/EP2017/055838, filed on Mar. 13, 2017, which claims priority to European Application No. 16160175.2, filed on Mar. 14, 2016 and European Application No. 16185173.8, filed on Aug. 22, 2016, applications which are incorporated herein by reference in their entirety.

FIELD OF THE INVENTION

The present invention relates to the field of medicinal therapeutics and treatment of infectious diseases. In particular, the present invention relates to the treatment of Severe Community Acquired Pneumonia (sCAP) and to a new pharmaceutical composition for use in the treatment of sCAP.

BACKGROUND

Community-acquired pneumonia (CAP) is a significant cause of morbidity and mortality in adults. In the United States, CAP is the number one cause of death from infectious diseases and the eighth leading cause of death, with an estimated 1.3 million hospitalizations each year (see e.g. Welte et al., 2015: Respir Med. 2015 June; 109 (6):758-67)). Severe Community Acquired Pneumonia (sCAP) is usually defined as CAP that requires intensive medical care, such as treatment with vasopressors or invasive mechanical ventilation. About 10% of hospitalized CAP patients can be classified as having sCAP. Mortality of sCAP patients admitted to the intensive care unit usually ranges from 23-58% depending on time of admission of the patient to hospital, and has not improved much in recent years despite the availability of improved broad-spectrum antibiotics. Severe CAP is a distinct clinical entity usually requiring intensive care unit (ICU) management. Severe CAP is caused by infection with a broad range of microorganisms including bacteria such as *Streptococcus pneumoniae, Haemophilus influenzae, Legionella pneumophilia, Staphylococcus aureus* and *Pseudomonas aeruginosa*, (cf. Cilloniz et al., Thorax. 2011 April; 66(4):340-6), as well as viruses and fungi. Thus, patients present with similar symptoms but with different underlying causes of the disease. In many cases, the causative pathogen cannot be identified, or is identified too late in order to apply a specific treatment in time, e.g. a specific antibiotic. A broad range therapeutic hence seems to be needed for adequate treatment of sCAP. The sCAP patient population partially overlaps with sepsis patient subpopulations but not all sCAP patients develop sepsis and sCAP patients form a subgroup within all sepsis patients.

A number of reports have been published on the possible effect of immunoglobulin preparations and concentrates for treating sepsis (e.g. Kreymann et al., Crit Care Med 2007 Vol. 35, No. 12; Que et al., 2014, Eur J Clin Microbiol Infect Dis 33:1861-1867), but none of them have shown real conclusive data either in favour or against benefit of using such treatment (cf. review and discussion by Werdan, 2006, Crit. Care Med. Vol. 34, No. 5 pp.1542-1544; Werdan 2012: Intensive-News Germany, Issue 4/12). The guideline of the German Sepsis Society (updated version of 2010, Reinhart et al., GMS German Medical Science 2010, Vol. 8, ISSN 1612-3174) differentiates between two groups of preparations: Preparations comprising solely IgG and preparations also enriched in IgM. The use of IgG preparations is not recommended in view of the negative results of clinical studies. In contrast, the use of IgM-enriched immunoglobulin preparations can be considered in treatment of adult patients with severe sepsis or septic shock. Similar recommendations can be found in international guidelines (Dellinger et al., Intensive Care Med 2013; 39(2): 165-228 and Crit Care Med 2013; 41(2): 580-637)). To the knowledge of the inventors, Pentaglobin (Biotest) is the only commercially available plasma-derived human immunoglobulin preparation enriched in both IgM and IgG (also comprising IgA) and has been used since the mid-nineteen-eighties to treat severe bacterial infections. Pentaglobin is a beta-propiolacton-modified immunoglobulin preparation which is high in IgG (76%) and also comprises IgM and IgA (12% each).

The influence of IgM and IgG and IgA levels on prognosis of septic patients is currently under discussion. Bermejo-Martin et al. reported that the simultaneous presence of low levels of the endogenous immunoglobulins IgG1, IgM, and IgA in plasma is associated with reduced survival in patients with severe sepsis or septic shock (Bermejo-Martin et al., J Intern Med 2014 276:404-412). The study refers to IgG1, not total IgG. The authors conclude that assessment of the concentrations of these immunoglobulins could improve the results of treatment with exogenous immunoglobulins in patients with sepsis. In contrast, Geier et al; 2015 (Med Klin Intensivmed Notfmed. 2015 Dec. 17), conclude they did not find a correlation between circulating levels of IgG, IgM, or IgA upon ICU admission and mortality in patients treated at a medical ICU and stated that no conclusions regarding the potential effects of therapeutic IVIG (intravenous immunoglobulin) administration could be drawn from their data. Also Venet et al., 2011 (International Immunopharmacology 11 (2011) 2086-2090) reported that although IgG and IgM levels were decreased in a majority of the sepsis patients treated with polyvalent immunoglobulin as adjunctive treatment, these alterations did not appear to be associated with increased mortality, morbidity or severity after septic shock. The study provides no final conclusion regarding the use of IVIG, but suggests further stratification. Giamarellos-Bourboulis and colleagues reported on the influence of circulating IgM levels in serum of patients with severe sepsis versus septic shock (Crit Care 2013 17:R247) and found that the distribution of IgM is lower among non-survivors. De la Torre et al. reported that low levels immunoglobulins, particularly total IgG and IgG2 were a common finding in patients with CAP compared to healthy controls (Resp Med 2013 107:2038-2045). Justel and coworkers concluded from their data that early assessment of IgM could contribute to guide clinical decisions in patients with severe pandemic influenza (J Clin Vir, 2013 58:564-567). Finally, Shankar-Hari et al., 2015 (Intensive Care Med. 2015 August; 41(8): 1393-401) reported that subnormal IgG levels on the day of sepsis diagnosis was not associated with an increased risk of death in adult patients with severe sepsis and/or septic shock by both fixed and random effect meta-analysis. They concluded that to allow IgG to be used as a stratification marker for IVIg therapy, further research relating endogenous immunoglobulin trajectory to illness characteristics and/or mortality is required, in additions to research exploring the mechanisms underlying a decrease in endogenous IgG level.

A new chemically unmodified IgM-enriched immunoglobulin preparation (designated BT086) has been developed by Biotest (cf. WO2011/131786 and WO2011/131787). BT086 is not treated and modified with beta-propiolacton. Therefore, differences in the properties and activities of both compounds are expected. Phase I pharmakokinetic data have been presented (Schmiedl et al., 2011, Pharmakokinetik und Vertraglichkeit des IgM-angereicherten Immunglobulin-Konzentrates BT086 bei gesunden Versuchspersonen nach Mehrfachgabe, and Schmiedl et al. 2011, Pharmakokinetik und Vertraglichkeit des IgM-angereicherten Immunglobulin-Konzentrates BT086 bei gesunden Versuchspersonen nach Einmalgabe mit Dosiseskalation, both were poster presentations at Verbund klinischer Pharmakologie in Deutschland, Zurich 2011). In a recent clinical trial sponsored by Biotest (CIGMA study, reported by Welte et al., 2015: Respir Med. 2015 June; 109 (6):758-67) IgM-enriched BT086 was used as an adjunctive therapy to treat sCAP patients. The treatment with BT086 showed a trend in reducing ventilator free days and 28-day mortality, but the study results were not statistically significant. (cf. Biotest AG Press release of Jun. 30, 2015).

CRP and PCT are inflammatory markers and both are used in the diagnosis and monitoring of inflammation, bacterial infection, tissue injury, or sepsis. The potential use of biomarkers such as CRP and PCT in assisting adjunctive therapy of sepsis in general has been discussed (Becze, Z., Molnar, Z., Fazakas, J., International Journal of Antimicrobial Agents 46 (2015) S13-S18). However, there has been no conclusive guidance as to the use of specific biomarker levels in guiding therapy.

In sCAP patients, Coelho and coworkers reported in 2012 (Critical Care 2012, 16:R53) that CRP could be used as a measure for therapy response since the chance of survival was significantly higher if CRP levels decreased by 30 to 70% after 72-96 hours of antibiotics treatment. PCT has been used in particular as a marker for bacterial infection. Jensen and coworkers (Crit Care Med 2006 Vol. 34, No. 10) reported on the use of PCT as a predictor for mortality in ICU patients, and speculated about PCT measurements to guide antibiotic therapy. Treatment with immunoglobulin preparations was not mentioned.

There is hence an unmet medical need for improved methods to treat sCAP with the aim to allow earlier weaning from invasive mechanical ventilation and to reduce morbidity and mortality in a more effective manner.

SUMMARY OF THE INVENTION

The present invention provides new therapeutic methods, tools, and guidance for treating sCAP patients using a human IgM-enriched human immunoglobulin preparation, in adjunctive treatment, i.e. as in addition to supportive and/or causal therapy such as invasive mechanical ventilation and/or antibacterial treatment.

Said human IgM-enriched immunoglobulin preparation differs from the established human immunoglobulin preparation Pentaglobin in that it has not been treated with beta-propiolactone. This results in a preparation that has different properties compared to Pentaglobin. E.g. it was found that batches of BT086 showed an about 10-fold increase in opsonisation of E. coli compared to Pentaglobin, although the IgM content in BT086 is increased merely two-fold compared to Pentaglobin.

The human IgM-enriched immunoglobulin preparation as used herein is plasma-derived, i.e. derived from pooled human blood plasma. As elaborated elsewhere in this specification, the preparation preferably comprises between 10 and 40% IgM by weight of total immunoglobulin content, and preferably between 10 and 35% IgA by weight of total immunoglobulin content and/or between 40 and 75% IgG by weight of total immunoglobulin content.

The inventors have now found that the overall outcome of the CIGMA study might have been affected by the heterogeneity of the sCAP patients. All patients had the symptoms and diagnosis of sCAP, but it was found that not all patients profited in the same way from the treatment with the IgM-enriched immunoglobulin preparation. Challenging in sCAP patients is that the cause of sCAP and the co-morbidities of the patients are heterogeneous and there is no simple way to distinguish between the underlying pathogens. Therefore, it would be advantageous to have simple parameters to identify patients which benefit more from the treatment with the IgM-enriched immunoglobulin preparation. Such parameters should ideally be independent from an identification of the underlying cause of the disease. To date, no information was available whether it would be possible to simply and quickly identify subgroups of sCAP patients which would benefit most of the treatment with said IgM-enriched immunoglobulin preparation. These findings are a step towards a more personalized treatment of sCAP patients, allowing better treatment decisions for the individual patient. In addition, the inventors identified different dosing schemes which can further improve the treatment with the IgM-enriched immunoglobulin preparation as defined herein.

In a first embodiment, the invention provides a human plasma-derived IgM-enriched immunoglobulin preparation for use in treating severe community acquired pneumonia (sCAP). Said immunoglobulin preparation is not chemically modified and is especially enriched in IgM, but preferably also in IgA immunoglobulins.

The IgM-enriched immunoglobulin preparation as defined herein is thought to act through a wide range of mechanisms interfering with pathophysiological processes which otherwise could lead to severe respiratory disturbances, severe sepsis, multi-organ failure and ultimately death of the patient. Besides neutralization of bacterial endotoxin and exotoxin, the IgM-enriched immunoglobulin preparation mediates increased recognition of pathogens by certain immune cells and promotes their destruction. In addition, the IgM-enriched immunoglobulin preparation can rebalance excessive immune responses and possesses anti-inflammatory properties.

The inventors have identified a number of parameters that can be used to select those sCAP patients that benefit the most of adjunctive therapy with the IgM-enriched immunoglobulin preparation as defined herein, in particular: 1) particular levels of inflammatory markers PCT or CRP and 2) particular levels of IgM and/or IgG and/or IgA at the onset of sCAP therapy or diagnosis.

The results found herein hence open new perspectives for using an IgM-enriched immunoglobulin preparation as an adjunctive treatment in a specific subset of sCAP patients, which can be easily selected by determining the level of certain blood biomarkers.

The present invention includes the following aspects:

Aspect 1. A human plasma-derived IgM-enriched, immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum CRP level of at least 50 mg/ml to at least 100 mg/l and/or a serum PCT level of at least 1.0 ng/ml to at least 15 ng/ml, preferably of at least 1.0 ng/ml to at least 5.0 ng/ml.

Aspect 2. The immunoglobulin preparation for use according to aspect 1, wherein the serum CRP-level is at least 50 mg/l, or at least 70 mg/l, or at least 75 mg/l, or at least 80 mg/l, or at least 100 mg/l, and/or wherein the serum PCT level is at least 1.0 ng/ml, or at least 1.5 ng/ml, or at least 2.0 ng/ml, or at least 5.0 ng/ml.

Aspect 3. The immunoglobulin preparation for use according to aspects 1 or 2, wherein said serum PCT and/or CRP level is present at the time of sCAP diagnosis, particularly is present at least once within 24 hours before to 24 hours after start of vasopressor therapy and/or start of invasive mechanical ventilation.

In some embodiments, said serum PCT and/or CRP level was measured at the pretreatment stage, such as at the moment of sCAP diagnosis, upon admission to the hospital, more particularly at day −1 of the start of sCAP causal and/or supportive therapy, more particularly at day −1 of antibiotic sCAP therapy or the start of vasopressor therapy or invasive mechanical ventilation. Preferably, the measurements are done prior to the intended start of treatment with the IgM-enriched immunoglobulin preparation as defined herein.

Aspect 4. The immunoglobulin preparation for use according to any of aspects 1 to 3, wherein the patient has a serum IgM level of equal to or lower than 0.4 to equal to or lower than 1.5 g/l, a serum IgG level of equal to or lower than 5 to equal to or lower than 10 g/l, and/or a serum IgA level of equal to or lower than 4.0 g/l, equal to or lower than 3.5 g/l, equal to or lower than 3 g/l, equal to or lower than 2.5 g/l, or equal to or lower than 2.0 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal to or lower than 7 g/l, or equal to or lower than 6 g/l.

Aspect 5. A human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum IgM level of equal to or lower than 0.5 g/l to equal to or lower than 1.5 g/l, and/or a serum IgG level of equal to or lower than 5 g/l to equal to or lower than 10 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal to or lower than 7 g/l, or equal to or lower than 6 g/l.

Aspect 6. A human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum IgA level of equal to or lower than 4.0 g/l, equal to or lower than 3.5 g/l, equal to or lower than 3 g/l, equal to or lower than 2.5 g/l, or equal to or lower than 2.0 g/l.

Aspect 7. The human IgM-enriched immunoglobulin preparation for use according to any one of aspects 1 to 6, wherein said adjunctive treatment is defined as a treatment in addition to causal and/or supportive sCAP therapy as defined herein elsewhere, more preferably in addition to antibiotic therapy as defined herein elsewhere.

Aspect 8. The human immunoglobulin preparation for use according to any of aspects 5 to 7, wherein said serum IgM, and/or IgG, and/or IgA level is present at the time of sCAP diagnosis, more particularly is present at least once within 24 hours before to 24 hours after the start of vasopressor therapy or start of invasive mechanical ventilation. In some embodiments, said serum IgM and/or IgG and/or IgA level was measured at the pretreatment stage such as at the moment of sCAP diagnosis, upon admission to the hospital, at the moment of sCAP diagnosis, more particularly at day −1 of the start of sCAP causal and/or supportive therapy, more particularly at day −1 of antibiotic therapy for sCAP or the start of vasopressor therapy or start of invasive mechanical ventilation (e.g. closest value to start of invasive mechanical ventilation).

Aspect 9. The immunoglobulin preparation for use according to any of aspects 1 to 8, wherein the immunoglobulin preparation has not been treated with beta-propiolactone.

Aspect 10. The human immunoglobulin preparation for use according to any of aspects 1 to 9, wherein the immunoglobulin preparation comprises from 10 to 40%, preferably from 18 to 28% by weight IgM of the total immunoglobulin content.

Aspect 11. The immunoglobulin preparation for use according to any of aspects 1 to 10, additionally comprising between 15-27% IgA of the total immunoglobulin content.

Aspect 12. The immunoglobulin preparation for use according to any of aspects 1 to 11, additionally comprising between 48-66% IgG, of the total immunoglobulin content.

Aspect 13. The immunoglobulin preparation for use according to any of aspects 1 to 12, having a total immunoglobulin content of at least 90%, preferably at least 95% by weight of the total protein content.

Aspect 14. The immunoglobulin preparation for use according to any of aspects 1 to 13, being in a composition, particularly a solution for intravenous administration. In particular, the invention provides a composition comprising the immunoglobulin preparation for use according to any of aspects 1 to 13, preferably a pharmaceutical composition. In particular embodiments, said composition is a solution for intravenous administration comprising between 20 and 100 gram immunoglobulin per liter solution, preferably between 40 and 60 gram immunoglobulin per liter solution, more preferably between 40 and 60 gram immunoglobulin per liter solution. In some embodiments, said solution is a 0.2 to 0.5 M glycine, preferably about 0.3 M glycine, preferably at a pH of between 4.3-4.7. In a preferred embodiment, said composition or solution has an average IgM concentration of 23% w/w of protein, which results in about 11.5 mg IgM/ml solution for intravenous administration.

Aspect 15. The immunoglobulin preparation for use according to any of aspects 1 to 14, wherein said immunoglobulin preparation is administered in 3 to 10 daily doses over 21 days, preferably with a first daily dose within 24 hours, preferably between 1 and 12 hours, after start of vasopressor therapy and/or start of invasive mechanical ventilation.

Aspect 16. The human immunoglobulin preparation for use according to any of aspects 1 to 15, wherein said immunoglobulin preparation is administered according to the following treatment regimen: a first daily dose (i.e. an initial dose) to be administered within 24 hours, preferably between 1 and 12 hours after start of vasopressor therapy and/or start of invasive mechanical ventilation, followed by 3 to 10, preferably 3 to 6, consecutive daily doses, and optionally one or more maintenance doses at 10 to 18 days after the first administration with said immunoglobulin preparation.

The expression "after start of vasopressor therapy and/or invasive mechanical ventilation" as used in these aspects means that either the start of vasopressor therapy or the start of invasive mechanical ventilation is sufficient to trigger the event. If both vasopressor therapy and invasive mechanical ventilation are initiated, then the event is triggered by the earlier of both.

Aspect 17. The human immunoglobulin preparation for use according to any of aspects 1 to 16, wherein the daily dosages are between 30 and 80 mg IgM/kg bodyweight, preferably between 35 and 65 mg IgM/kg bodyweight, more preferably between 40 and 45 mg IgM/kg bodyweight.

Aspect 18. The human immunoglobulin preparation for use according to any of aspects 1 to 17, wherein the initial dose is higher than the daily dosages such as wherein said initial dose is between 50 and 80 mg IgM/kg bodyweight, preferably between 60 and 65 mg IgM/kg bodyweight. In some embodiments the initial dose is about 1.5 times the daily dose as referred herein, but not exceeding 80 mg IgM/kg bodyweight.

Aspect 19. The human immunoglobulin preparation for use according to any of aspects 1 to 18, wherein a maintenance dose of between 30 and 80 mg IgM/kg bodyweight, preferably between 35 and 65 mg IgM/kg bodyweight, more preferably between 40 and 45 mg IgM/kg bodyweight or between 60 and 65 mg IgM/kg bodyweight is administered.

Aspect 20. The human immunoglobulin preparation for use according to any of aspects 1 to 19, wherein the infusion rate is equal to or less than 6 mg IgM/min, more preferably the initial infusion rate is equal to or less than 2 mg IgM/min. In some embodiments, the initial infusion rate is 0.1 ml IgM solution as defined herein per minute. Said infusion rate can be increased in steps of 0.1 ml every 10 minutes up to a maximum infusion rate of 0.5 ml IgM solution as defined herein per minute.

Aspect 21. The human immunoglobulin preparation for use according to any of aspects 1 to 20, characterized in that the number of plasma donors is at least 500, at least 1500, more preferably at least 2500.

Aspect 22. The human immunoglobulin preparation for use according to any of aspects 1 to 21, wherein the patient is male and/or wherein the patient is not older than 65 years.

Aspect 23. A container comprising the IgM-enriched immunoglobulin preparation or pharmaceutical composition for use according to anyone of the previous aspects or comprising the composition according to aspect 14. In some embodiments, such a container can be a vial with a rubber stopper comprising a liquid formulation, preferably with a pierceable stopper. Alternatively, said container can be a fluid bag, suitable for use in intravenous administration, typically comprising the immunoglobulin preparation formulated in a solution for intravenous administration.

Aspect 24. A package or kit comprising a single or multiple container(s) according to aspect 23, and instructions for administration, preferably with instructions for administration according to the administration scheme defined in any one of aspects 14 to 19.

Aspect 25. A method for identifying an sCAP patient who would benefit from adjunctive treatment with a human plasma-derived IgM-enriched immunoglobulin preparation, said immunoglobulin preparation not having been chemically modified or treated with beta-propiolactone, comprising the steps of determining serum CRP level, and/or serum PCT level, and/or serum IgM level, and/or serum IgG level, and/or serum IgA level, or any combination thereof in a blood sample of the patient, wherein any one or more of: (1) a serum CRP level of at least 50 mg/l to at least 100 mg/l; (2) a serum PCT level of at least 1.0 to at least 5.0 ng/ml; (3) a serum IgM level of equal to or lower than 0.5 to at least 1.5 g/l; (4) a serum IgG level of equal to or lower than 5 to at least 10 g/l such as serum IgG level of maximum 10 g/l, preferably of maximum 9 g/l, preferably of maximum 8 g/l, more preferably of maximum 7 g/l; (5) a serum IgA level of maximum 4.0 g/l, preferably maximum 3.5 g/l, preferably maximum 3.0 g/l, preferably maximum 2.5 g/l, or preferably maximum 2.0 g/l, is indicative that the patient may benefit, is likely to benefit, or will benefit from such treatment.

In some embodiments, a serum IgM level which is equal to or lower than 1.0 g/l, equal to or lower than 0.8 g/l, or equal to or lower than 0.7 g/l, or equal to or lower than 0.6 g/l, or equal to or lower than 0.5 g/l, or equal to or lower than 0.4 g/l, and/or an IgG level which is equal to or lower than 9 g/l, or equal to or lower than 8 g/l, or equal to or lower than 7 g/l, or equal to or lower than 6 g/l, is indicative that the patient may benefit, is likely to benefit, or will benefit from such treatment.

In some embodiments, when said serum, CRP, PCT, IgM, IgG, or IgA level is present at the time of sCAP diagnosis, particularly when said level is present at least once within 24 hours before to 24 hours after start of vasopressor therapy and/or start of invasive mechanical ventilation, it is indicative that the patient may benefit, is likely to benefit, or will benefit from such treatment.

In some embodiments, the measurement of said PCT, CRP, IgM, IgG or IgA levels is done prior to the intended start of treatment with the IgM enriched immunoglobulin preparation as defined herein. Particularly, the measurement of said PCT, CRP, IgM, IgG, or IgA levels is done at the pretreatment stage such as at the moment of sCAP diagnosis, upon admission to the hospital, more particularly at day −1 of the start of sCAP causal and/or supportive therapy, more particularly at day −1 of antibiotic therapy for sCAP or the start of vasopressor therapy or start of invasive mechanical ventilation (e.g. closest value to start of invasive mechanical ventilation). Preferably, the measurements should be done prior to the intended start of treatment with the IgM-enriched immunoglobulin preparation as defined herein.

Aspect 26. A method of treating sCAP in a patient in need thereof, comprising the administration of a human plasma-derived IgM-enriched immunoglobulin preparation, said immunoglobulin preparation not having been chemically modified and/or treated with beta-propiolactone, wherein said sCAP patient has a serum CRP level of at least 50 mg/ml to at least 100 mg/l and/or a serum PCT level of at least 1.0 ng/ml to at least 5.0 ng/ml.

Aspect 27. The method according to aspect 26, wherein the serum CRP-level is at least 50 mg/l, or at least 70 mg/l, or at least 75 mg/l, or at least 80 mg/l, or at least 100 mg/l, and/or wherein the serum PCT level is at least 1.0 ng/ml, or at least 1.5 ng/ml, or at least 2.0 ng/ml, or at least 5.0 ng/ml.

Aspect 28. The method according to aspect 26 or 27, wherein said adjunctive treatment is defined as a treatment in addition to causal and/or supportive sCAP therapy as defined herein elsewhere, more preferably in addition to antibiotic therapy as defined herein elsewhere.

Aspect 29. The method according to any of aspects 26 to 28, wherein said serum PCT and/or CRP level is present at the time of sCAP diagnosis, particularly is present at least once within 24 hours before to 24 hours after start of vasopressor therapy and/or start of invasive mechanical ventilation.

In some embodiments, said serum PCT and/or CRP level was measured at the pretreatment stage, such as at the moment of sCAP diagnosis, upon admission to the hospital, more particularly at day −1 of the start of sCAP causal and/or supportive therapy, more particularly at day −1 of antibiotic sCAP therapy or the start of vasopressor therapy or start of invasive mechanical ventilation. Preferably, the measurements are done prior to the intended start of treatment with the IgM-enriched immunoglobulin preparation as defined herein.

Aspect 30. The method according to any of aspects 26 to 29, wherein the patient has a serum IgM level of equal to or lower than 0.5 to equal to or lower than 1.5 g/l; a serum IgG level of equal to or lower than 5 to equal to or lower than 10 g/l; and/or a serum IgA level of equal to or lower than 4.0 g/l, equal to or lower than 3.5 g/l, equal to or lower than 3 g/l, equal to or lower than 2.5 g/l, or equal to or lower than 2.0 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal to or lower than 7 g/l, or equal to or lower than 6 g/l.

Aspect 31. A method of treating sCAP in a patient in need thereof, comprising the administration of a human plasma-derived IgM-enriched immunoglobulin preparation, said immunoglobulin preparation not having been chemically modified and/or treated with beta-propiolactone, wherein said patient has a serum IgM level of equal to or lower than 0.5 g/l to equal or lower than 1.5 g/l; a serum IgG level of equal to or lower than 5 to equal to or lower than 10 g/l; and/or a serum IgA level of equal to or lower than 4.0 g/l, equal to or lower than 3.5 g/l, equal to or lower than 3 g/l, equal to or lower than 2.5 g/l, or equal to or lower than 2.0 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal to or lower than 7 g/l, or equal to or lower than 6 g/l.

Aspect 32. The method according to aspect 31, wherein said adjunctive treatment is defined as a treatment in addition to causal and/or supportive sCAP therapy as defined herein elsewhere, more preferably in addition to antibiotic therapy as defined herein elsewhere.

Aspect 33. The method according to aspect 31 or 32, wherein said serum IgM, IgG, and/or IgA level is present at the time of sCAP diagnosis, more particularly is present at least once within 24 hours before to 24 hours after the start of vasopressor therapy or start of invasive mechanical ventilation. In some embodiments, said serum IgM, IgG, and/or serum IgA level was measured at the pretreatment stage such as at the moment of sCAP diagnosis, upon admission to the hospital, at the moment of sCAP diagnosis, more particularly at day −1 of the start of sCAP causal and/or supportive therapy, more particularly at day −1 of antibiotic therapy for sCAP or the start of vasopressor therapy or invasive mechanical ventilation (e.g. closest value to start of invasive mechanical ventilation).

Aspect 34. The method according to any of aspects 26 to 33, wherein the immunoglobulin preparation comprises from 10 to 40%, preferably from 18 to 28% by weight IgM of the total immunoglobulin content.

Aspect 35. The method according to any of aspects 26 to 34, wherein the immunoglobulin preparation additionally comprises between 15-27% IgA of the total immunoglobulin content.

Aspect 36. The method according to any of aspects 26 to 35, wherein the human immunoglobulin preparation additionally comprises between 48-66% IgG, of the total immunoglobulin content.

Aspect 37. The method according to any of aspects 26 to 36, wherein said preparation has a total immunoglobulin content of at least 90%, preferably at least 95% by weight of the total protein content.

Aspect 38. The method according to any of aspects 26 to 37, wherein said immunoglobulin preparation is present in a composition, preferably in a pharmaceutical composition. In some embodiments, said composition or pharmaceutical composition is a solution for intravenous administration comprising between 40 and 100 gram immunoglobulin per liter solution, preferably between 40 and 60 gram immunoglobulin per liter solution. In some embodiments, said solution is a 0.2 to 0.5 M glycine, preferably at a pH of between 4.3-4.7. In a preferred embodiment, said solution has an average IgM concentration of 23% w/w of protein, which results in about 11.5 mg IgM/ml solution for intravenous administration.

Aspect 39. The method according to any of aspects 26 to 38, wherein said immunoglobulin preparation is administered in 3 to 10 daily doses over 21 days, preferably with a first daily dose within 24 hours, preferably between 1 and 12 hours, after start of vasopressor therapy and/or start of invasive mechanical ventilation.

Aspect 40. The method according to any of aspects 26 to 39, wherein said immunoglobulin preparation is administered according to the following treatment regimen: a first daily dose (i.e. an initial dose) to be administered within 24 hours, preferably between 1 and 12 hours after start of vasopressor therapy and/or start of invasive mechanical ventilation, followed by 3 to 10, preferably 3 to 6, such as 4 or 5, consecutive daily doses, and optionally one or more maintenance doses at 10 to 18 days after the first administration with said immunoglobulin preparation.

The expression "after start of vasopressor therapy and/or invasive mechanical ventilation" as used herein means that either the start of vasopressor therapy or the start of invasive mechanical ventilation is sufficient to trigger the event. If both vasopressor therapy and invasive mechanical ventilation are initiated, then the event is triggered by the earlier of both.

Aspect 41. The method according to any of aspects 26 to 40, wherein the daily dosages are between 30 and 80 mg IgM/kg bodyweight, preferably between 35 and 65 mg IgM/kg bodyweight, more preferably between 40 and 45 mg IgM/kg bodyweight.

Aspect 42. The method according to any of aspects 26 to 41, wherein the initial dose is higher than the daily dosages such as wherein said initial dose is between 50 and 80 mg IgM/kg bodyweight, preferably between 60 and 65 mg IgM/kg bodyweight. In some embodiments the initial dose is about 1.5 times the daily dose as referred herein, but not exceeding 80 mg IgM/kg bodyweight.

Aspect 43. The method according to any of aspects 26 to 42, wherein a maintenance dose of between 30 and 80 mg IgM/kg bodyweight, preferably between 35 and 65 mg IgM/kg bodyweight, more preferably between 40 and 45 mg IgM/kg bodyweight or between 60 and 65 mg IgM/kg bodyweight is administered.

Aspect 44. The method according to any of aspects 26 to 43, wherein the infusion rate is equal or less than 6 mg IgM/min, more preferably the initial infusion rate is equal to or less than 2 mg IgM/min. In some embodiments, the initial infusion rate is 0.1 ml IgM solution as defined herein per minute. Said infusion rate can be increased in steps of 0.1 ml every 10 minutes up to a maximum infusion rate of 0.5 ml IgM solution as defined herein per minute.

Aspect 45. The method according to any of aspects 26 to 44, characterized in that the number of plasma donors is at least 500, at least 1500, more preferably at least 2500.

Aspect 46. The method according to any of aspects 26 to 45, wherein the patient is male and/or wherein the patient is not older than 65 years.

Aspect 47. Use of a human plasma-derived IgM-enriched immunoglobulin preparation, said immunoglobulin preparation not having been chemically modified and/or treated with beta-propiolactone, for the manufacturing of a medicament for use in adjunctive treatment of severe Community Acquired Pneumonia (sCAP) in a patient, wherein said patient has a serum CRP level of at least 50 mg/ml to at least 100 mg/l and/or a serum PCT level of at least 1.0 ng/ml to at least 5.0 ng/ml.

Aspect 48. The use according to aspect 47, wherein the serum CRP-level is at least 50 mg/l, or at least 70 mg/l, or at least 75 mg/l, or at least 80 mg/l, or at least 100 mg/l, and/or wherein the serum PCT level is at least 1.0 ng/ml, or at least 1.5 ng/ml, or at least 2.0 ng/ml, or at least 5.0 ng/ml.

Aspect 49. The use according to aspects 47 or 48, wherein said serum PCT and/or CRP level is present at the time of sCAP diagnosis, particularly is present at least once within 24 hours before to 24 hours after start of vasopressor therapy and/or start of invasive mechanical ventilation.

In some embodiments, said serum PCT and/or CRP level was measured at the pretreatment stage, such as at the moment of sCAP diagnosis, upon admission to the hospital, more particularly at day −1 of the start of sCAP causal and/or supportive therapy, more particularly at day −1 of antibiotic sCAP therapy or the start of vasopressor therapy or start of invasive mechanical ventilation. Preferably, the measurements are done prior to the intended start of treatment with the IgM-enriched immunoglobulin preparation as defined herein.

Aspect 50. The use according to any of aspects 47 to 49, wherein the patient has a serum IgM level of equal to or lower than 0.5 to equal to or lower than 1.5 g/l; a serum IgG level of equal to or lower than 5 to equal to or lower than 10 g/l; and/or a serum IgA level of equal to or lower than 4.0 g/l, equal to or lower than 3.5 g/l, equal to or lower than 3 g/l, equal to or lower than 2.5 g/l, or equal to or lower than 2.0 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal to or lower than 7 g/l, or equal to or lower than 6 g/l.

Aspect 51. Use of a human plasma-derived IgM-enriched immunoglobulin preparation, said immunoglobulin preparation not having been chemically modified and/or treated with beta-propiolactone, for the manufacturing of a medicament for use in adjunctive treatment of severe Community Acquired Pneumonia (sCAP) in a patient, wherein said patient has a serum IgM level of equal to or lower than 0.5 to equal to or lower than 1.5 g/l; a serum IgG level of equal to or lower than 5 to equal to or lower than 10 g/l; and/or a serum IgA level of equal to or lower than 4.0 g/l, equal to or lower than 3.5 g/l, equal to or lower than 3 g/l, equal to or lower than 2.5 g/l, or equal to or lower than 2.0 g/l.

In some embodiments, said serum IgM level is equal to or lower than 1.0 g/l, equal to or lower than 0.8 g/l, or equal to or lower than 0.7 g/l, or equal to or lower than 0.6 g/l, or equal to or lower than 0.5 g/l, and/or wherein the IgG level is equal to or lower than 9 g/l, or equal to or lower than 8 g/l, or equal toor lower than 7 g/l, or equal to or lower than 6 g/l.

Aspect 52. The use according to aspect 51, wherein said adjunctive treatment is defined as a treatment in addition to causal and/or supportive sCAP therapy as defined herein elsewhere, more preferably in addition to antibiotic therapy as defined herein elsewhere.

Aspect 53. The use according to aspect 51 or 52, wherein said serum IgM, IgG, and/or IgA level is present at the time of sCAP diagnosis, more particularly is present at least once within 24 hours before to 24 hours after the start of vasopressor therapy or start of invasive mechanical ventilation. In some embodiments, said serum IgM, IgG and/or IgA level was measured at the pretreatment stage such as at the moment of sCAP diagnosis, upon admission to the hospital, at the moment of sCAP diagnosis, more particularly at day −1 of the start of sCAP causal and/or supportive therapy, more particularly at day −1 of antibiotic therapy for sCAP or the start of vasopressor therapy or start of invasive mechanical ventilation (e.g. closest value to start of invasive mechanical ventilation).

Aspect 54. The use according to any of aspects 47 to 53, wherein the immunoglobulin preparation has not been treated with beta-propiolactone.

Aspect 55. The use according to anyone of aspects 47 to 53, wherein the immunoglobulin preparation comprises from 10 to 40%, preferably from 18 to 28% by weight IgM of the total immunoglobulin content.

Aspect 56. The use according to any of aspects 47 to 55, additionally comprising between 15-27% IgA of the total immunoglobulin content.

Aspect 57. The use according to any of aspects 47 to 56, additionally comprising between 48-66% IgG, of the total immunoglobulin content.

Aspect 58. The use according to any of aspects 47 to 57, having a total immunoglobulin content of at least 90%, preferably at least 95% by weight of the total protein content.

Aspect 59. The use according to any of aspects 47 to 58, wherein said immunoglobulin preparation is present in a composition, preferably a pharmaceutical composition. In some embodiments, said composition or pharmaceutical composition is a solution for intravenous administration comprising between 40 and 100 gram immunoglobulin per liter solution, preferably between 40 and 60 gram immunoglobulin per liter solution. In some embodiments, said solution is a 0.2 to 0.5 M glycine, preferably at a pH of between 4.3-4.7. In a preferred embodiment, said solution has an average IgM concentration of 23% w/w of protein, which results in about 11.5 mg IgM/ml solution for intravenous administration.

Aspect 60. The use according to any of aspects 47 to 59, wherein said immunoglobulin preparation is administered in 3 to 10 daily doses over 21 days, preferably with a first daily dose within 24 hours, preferably between 1 and 12 hours, after start of vasopressor therapy and/or invasive mechanical ventilation.

Aspect 61. The use according to any of aspects 47 to 60, wherein said immunoglobulin preparation is administered according to the following treatment regimen: a first daily dose (i.e. an initial dose) to be administered within 24 hours, preferably between 1 and 12 hours after start of vasopressor therapy and/or start of invasive mechanical ventilation, followed by 3 to 10, preferably 3 to 6, such as 4 or 5, consecutive daily doses, and optionally one or more maintenance doses at 10 to 18 days after the first administration with said immunoglobulin preparation.

The expression "after start of vasopressor therapy and/or start of invasive mechanical ventilation" as used in these aspects means that either the start of vasopressor therapy or the start of invasive mechanical ventilation is sufficient to trigger the event. If both vasopressor therapy and invasive mechanical ventilation are initiated, then the event is triggered by the earlier of both.

Aspect 62. The use according to any of aspects 47 to 61, wherein the daily dosages are between 30 and 80 mg IgM/kg bodyweight, preferably between 35 and 65 mg IgM/kg bodyweight, more preferably between 40 and 45 mg IgM/kg bodyweight.

Aspect 63. The use according to any of aspects 47 to 62, wherein the initial dose is higher than the daily dosages such as wherein said initial dose is between 50 and 80 mg IgM/kg, preferably between 60 and 65 mg IgM/kg bodyweight. In some embodiments the initial dose is about 1.5 times the daily dose as referred herein, but not exceeding 80 mg IgM/kg bodyweight.

Aspect 64. The use according to any of aspects 47 to 63, wherein a maintenance dose of between 30 and 80 mg IgM/kg bodyweight, preferably between 35 and 65 mg IgM/kg bodyweight, more preferably between 40 and 45 mg IgM/kg bodyweight or between 60 and 65 mg IgM/kg bodyweight is administered.

Aspect 65. The use according to any of aspects 47 to 64, wherein the infusion rate is equal to or less than 6 mg IgM/min, more preferably the initial infusion rate is equal to or less than 2 mg IgM/min. In some embodiments, the initial infusion rate is 0.1 ml IgM solution as defined herein per minute. Said infusion rate can be increased in steps of 0.1 ml every 10 minutes up to a maximum infusion rate of 0.5 ml IgM solution as defined herein per minute.

Aspect 66. The use according to any of aspects 47 to 65, characterized in that the number of plasma donors is at least 500, at least 1500, more preferably at least 2500.

Aspect 67. The use according to any of aspects 47 to 66, wherein the patient is male and/or wherein the patient is not older than 65 years.

DETAILED DESCRIPTION OF THE INVENTION

Figure 1:
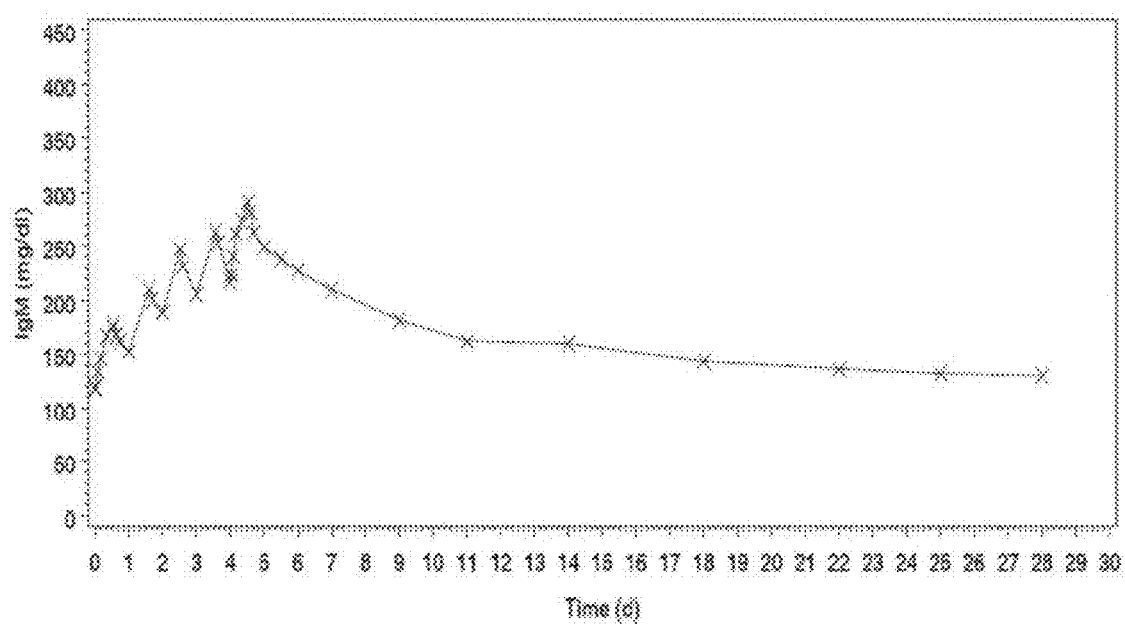
FIG. 1 shows IgM levels in healthy subjects. 5 daily administrations of 42 mg/kg bodyweight of IgM-enriched immunoglobulin preparation BT086. Mean serum concentration versus time profiles of total IgM following repeated intravenous infusions of BT086. IgM levels in healthy subjects reached after 5 daily administrations of 42 mg/kg bodyweight of the IgM-enriched immunoglobulin preparation (BT086) as described herein.

The present invention will be described with respect to particular embodiments but the invention is not limited thereto but only by the claims. Any reference signs in the claims shall not be construed as limiting the scope. The following terms or definitions are provided solely to aid in the understanding of the invention. Unless specifically defined herein, all terms used herein have the same meaning as they would to one skilled in the art of the present invention. The definitions provided herein should not be construed to have a scope less than the one understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the singular forms 'a', 'an', and the include both singular and plural referents unless the context clearly dictates otherwise. The term "any" when used in relation to aspects, claims or embodiments as used herein refers to any single one (i.e. anyone) as well as to all combinations of said aspects, claims or embodiments referred to.

The terms 'comprising', 'comprises' and 'comprised of' as used herein are synonymous with 'including', 'includes' or 'containing', 'contains', and are inclusive or open-ended and do not exclude additional, non-recited members, elements or method steps. Said terms also encompass the embodiments "consisting essentially of" and "consisting of".

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

As used herein, the term "for use" as used in "preparation for use in treatment of a disease" shall disclose also the corresponding method of treatment and the corresponding use of a preparation for the manufacture of a medicament for the treatment of a disease".

The term "Community Acquired Pneumonia" or "CAP" is known to the person skilled in the art, see e.g. the IDSA/ATS Guidelines for CAP in Adults (CID 2007:44 (Suppl 2) S27). In particular, the term refers to pneumonia acquired outside the hospital. This is in contrast to Hospital Acquired Pneumonia (HAP) or Ventilator-associated pneumonia (VAP). HAP refers to pneumonia acquired during or after hospitalization for another illness or procedure with onset at least 48 to 72 hours after admission. VAP is a subset of HAP that occurs after at least 48 hours of intubation and mechanical ventilation. HAP is considered to be more heterogeneous than CAP and may also be caused by a different pathogen spectrum. CAP is caused by infection with a broad range of microorganisms including bacteria such as *Streptococcus pneumoniae, Haemophilus influenzae, Legionella pneumophila, Staphylococcus aureus* and *Pseudomonas aeruginosa*, (cf. Cilloniz et al., Thorax. 2011 April; 66(4):340-6), as well as viruses and fungi.

The term "severe Community Acquired Pneumonia" or "sCAP" is known to the skilled person. In particular, the term "severe Community Acquired Pneumonia" or "sCAP" refers to the subgroup of Community Acquired Pneumonia patients that require intensive care. The Infectious Disease Society of America (IDSA) and the American Thoracic Society (ATS) have issued guidelines on the management of CAP including a definition of sCAP (cf. Mandell et al., 2007, Infectious Diseases Society of America/American Thoracic Society Consensus Guidelines on the Management of Community-Acquired Pneumonia in Adults, Clin. Inf. Dis. 2007: 44:S27-72 (Suppl 2), Table 4). According to the IDSA/ATS guidelines sCAP is defined as CAP requiring intensive care. Admission to the intensive care unit is recommended if the CAP patient shows one or both of two major criteria, or presence of three minor criteria from the list as follows:

Minor Criteria[a]
Respiratory rate[b] above or equal to 30 breaths/min
PaO2/FiO2 ratio[b] below or equal to 250
Multilobar infiltrates
Confusion/disorientation
Uremia (BUN level, above or equal to 20 mg/dL)
Leukopenia[c] (WBC count, below 4000 cells/mm$^3$)
Thrombocytopenia (platelet count, below 100,000 cells/mm$^3$)
Hypothermia (core temperature, below 36° C.)
Hypotension requiring aggressive fluid resuscitation

[a] Other criteria to consider include hypoglycemia (in nondiabetic patients), acute alcoholism/alcoholic withdrawal, hyponatremia, unexplained metabolic acidosis or elevated lactate level, cirrhosis, and asplenia.
[b] A need for noninvasive ventilation can substitute for a respiratory rate above 30 breaths/min or a PaO$_2$/FiO$_2$ ratio below 250.
[c] As a result of infection alone.

Major Criteria
Invasive mechanical ventilation
Septic shock with the need for vasopressors
Abbreviations in the above context:
BUN, blood urea nitrogen; PaO$_2$/FiO$_2$, arterial oxygen pressure/fraction of inspired oxygen; WBC, white blood cell.

More particularly, a patient having sCAP according to the present invention, fulfils the following criteria:

1) Need for invasive mechanical ventilation or need for treatment with vasopressors, particularly need for endotracheal ventilation or ventilation by tracheostomy, most particularly need for endotracheal ventilation
2) Patient receiving antibiotic treatment for pneumonia
3) Patient must have signs and symptoms of pneumonia. Particularly at least one of the following signs: new or increased cough; production of purulent sputum or change in sputum characteristics; dyspnea or tachypnea (respiratory rate >20 breaths/minute); pleuritic chest pain; auscultatory findings on pulmonary examination of rales and/or crackles and/or evidence of pulmonary consolidation (e.g. dullness on percussion, bronchial breath sounds, or egophony).
4) Preferably also radiological (or other imaging technique) evidence of pneumonia
5) Pneumonia has been acquired outside the hospital. In hospital admitted patients, pneumonia has been diagnosed a maximum of 72 hours, particularly a maximum of 48 hours after admission.

sCAP according to the present invention also includes patients from nursing homes or similar institutions.

It is estimated that roughly about 80% of all sCAP patients receiving invasive mechanical ventilation also require therapy with vasopressors. Roughly about 60% of all sCAP patients are treated with vasopressors in absence of invasive mechanical ventilation.

The immunoglobulin preparation for use as an adjunctive therapy for treating sCAP as defined herein is plasma-derived. The term "plasma-derived" is known to the skilled person. Particularly, according to the present invention the term "plasma-derived" means that the preparation is derived from blood plasma of a multitude of different healthy human donors. Such plasma-derived products are generally known in the art. Preferably, at least 70%, more preferably at least 90%, more preferably at least 95% of the proteins in the preparation are derived from human blood plasma. Optionally, the plasma-derived preparation is substantially free from recombinant proteins. However, the preparation may also be present in the form of a composition comprising further excipients as described herein elsewhere. It is also contemplated to use the preparation in the form of a composition comprising a secretory component such as the extracellular portion of the polymeric immunoglobulin receptor pIgR (WO2013/132052 (assigned to CSL Behring), U.S. Pat. No. 7,794,721 (Simon)). Such secretory component may be recombinantly produced.

Typically, the plasma-derived preparation is derived from pooled blood plasma. The term "pooled blood plasma" as used herein encompasses the pooling of plasma from different subjects, but does not mean that the pool is actually manufactured as a single pool. It may be advantageous to manufacture the pool in subpools. The pooled blood plasma thus can be blended from subpools or at later stages of manufacturing the human immunoglobulin preparation. Indeed, also the human immunoglobulin preparation or the final composition may be blended from different human immunoglobulin preparations or compositions. Preferably, the plasma pool contains plasma from at least 500, at least 1000, 2000, 2500, 3000, 4000, or at least 5000 donors. The number of donors can hence vary between 500 to over 5000, preferably between 2500 and 5000 donors, more preferably more than 5000 donors.

The immunoglobulin preparation as defined herein comprises a substantially pure human plasma protein preparation, wherein at least 93%, preferably at least 95% of the protein content is immunoglobulin. The immunoglobulin preparation as defined herein hence comprises naturally occurring immunoglobulins obtained through pooling and purification of blood plasma from different donors. The number of donors and the difference in donor antibody spectrum results in a pool of antibodies that have a great diversity towards different pneumonia causing agents such as bacteria, viruses and fungi, The IgM-enriched immunoglobulin preparation according to the present invention comprises IgM, IgA, and IgG. The total content of immunoglobulins in the IgM-enriched preparation is preferably at least 85%, more particularly at least 90%, most particularly at least 95% of the total protein content.

In addition the immunoglobulin preparation used in the context of the present invention has not been chemically modified. In the context of the present invention "not having been chemically modified" or "chemically unmodified" shall mean that the immunoglobulin preparation has not been intentionally modified, in particular the preparation has not been treated by adding agents which covalently modify the immunoglobulins. Such agents are known and include alkylating agents (such as beta-propiolactone) or proteases such as pepsin. The person skilled in the art will appreciate that in any purification or production process some unintentional modification may occur, such as polymerization, aggregation, oxidation, de-amidation, or conformational changes. Also some unintentional fragmentation may occur due to proteases present in the plasma. Also UV-treatment may lead to some modification of the immunoglobulin molecules. More specifically, the immunoglobulin preparation used in the context of the invention has not been treated by adding beta-propiolactone or adding enzymes such as proteases, more particularly the immunoglobulin preparation has not been treated with beta-propiolactone.

Such treatments, e.g. the treatment with beta-propiolactone, may be used for viral inactivation, see also EP001319 (Biotest). Beta-propiolactone leads to alkylation of proteins and thus can change their conformation and properties. The term "not having been treated with beta-propiolactone" or "not treated with beta-propiolactone" means particularly that no beta-propiolactone has been added during the manufacuring process of the IgM enriched immunoglobulin preparation, in particular that during all times of the process less than 0.01 ml beta-propiolactone/40 g total immunoglobulin, more particularly less than 0.001 ml beta-propiolactone, has been present in the immunoglobulin preparation at any time during the manufacturing process. Chemical modification may lead to partial loss or change of activity. Therefore, the immunoglobulin preparation according to the present invention is considered to be different from other IgM and IgA containing immunoglobulin preparations, such as Pentaglobin (which is treated with about 1.25 ml beta-propiolactone/40 g/l total immunoglobulin). For example, a chemically unmodified IgM preparation shows a higher activity in opsonization compared to a preparation that has been treated with beta-propiolactone. Similarly, the IgM-enriched immunoglobulin preparation according to the present invention has preferably not been pasteurized or heat-treated as this may lead to undesired aggregate formation or denaturation, resulting in a loss of activity. Also the IgM-enriched immunoglobulin preparation according to the present invention has preferably not been enzymatically modified e.g. by pepsin as this may lead a loss of activity.

Alternative viral inactivation treatments are available to the skilled person and can be used for the immunoglobulin preparation used in the context of the present invention, e.g. treatment with octanoic acid (preferably using a vibrating agitator), UV irradiation, and/or nanofiltration (see e.g. International patent application WO2011/131786 (Biotest) herein incorporated in its entirety by reference).

The IgM in the IgM-enriched immunoglobulin preparation mediates a plurality of biological activities. IgM is particularly active in opsonisation and complement activation. IgM is also able to neutralize endo- and exotoxins. Opsonisation is the process by which a pathogen is coated with an antibody and thus marked for destruction by the immune system. Being secreted as a pentamer, IgM possesses high avidity, and is particularly effective at complement activation. IgM contributes to opsonisation by activating complement and causing complement factor C3b to bind to the antigen. IgM is the first class of immunoglobulin being produced after activation of a B-cell. In contrast to IgG, the IgM molecule contains a J-chain and is considered to be secretable.

The IgA in the IgM-enriched immunoglobulin preparation mediates a plurality of biological activities. IgA interacts particularly with the Fc receptors called on immune effector cells initiating inflammatory reactions, antibody-dependent cell-mediated cytotoxicity (ADCC), degranulation of eosinophils and basophils, phagocytosis by monocytes, macrophages, and neutrophils, and triggering of respiratory burst activity by polymorphonuclear leukocytes. IgA may also scavenge activated complement factors.

The IgG in the IgM-enriched immunoglobulin preparation also mediates opsonisation and additionally also binds and neutralizes toxins, plays a role in antibody-dependent cell-mediated cytotoxicity (ADCC). IgG binds different complement factors. IgG has also immune modulating properties, which contribute to the activity profile of the IgM-enriched preparation according to the invention. In addition, a certain amount of IgG in the immunoglobulin preparation may improve the stability of the preparation in liquid form. In contrast to IgG, the IgA molecule contains a J-chain and is considered to be secretable.

The IgM-enriched immunoglobulin preparation should comprise a certain amount of IgM. The term "IgM-enriched" means that the content of IgM may range from 5 to 70% IgM, preferably 10 to 40%, more preferably 17 to 35%, of the total immunoglobulin content by weight (w/w), and preferably a concentration of at least 5 g/l IgM in the preparation. A low content of IgM may not be desirable in view of the necessary biological activity. On the other hand, a certain amount of IgG may be desirable as it improves stability of the preparation in liquid form. Preparations comprising more than e.g. 40% IgM of the total immunoglobulin content can be prepared e.g. in lyophilized form. Preferably, the IgM-enriched immunoglobulin preparation has the following composition (such composition is particularly preferred if the preparation is a liquid preparation):

from 10 to 40%, preferably 17 to 35%, more preferably 18% and 28%, more preferably 20 to 26%, more preferably 22 to 24% immunoglobulin M of the total immunoglobulin content by weight (w/w), from 10 to 35%, preferably 15% to 27%, more preferably 20 to 25%, more preferably 22 to 24% immunoglobulin A of the total immunoglobulin content by weight (w/w), and from 40% to 75%, preferably from 48% to 66%, more preferably 53 to 55% immunoglobulin G of the total immunoglobulin content by weight (w/w).

Preferably, the concentration of IgM in the preparation is at least 5 g/l, more preferably at least 7 g/l, more preferably at least 8 g/l, more preferably at least 10 g/l.

In the prior art, immunoglobulin preparations with an even higher content of IgM are known (see e.g. EP0352500), but a certain content of IgG is advantageous as may improve stability in liquid form and may also exert useful biological functions.

The percentage values can be determined by nephelometry or by immunoprecipitation according to Ph. Eur. 7.0, 2011; 2.2.1 and 2.7.1).

Exemplary IgM-enriched immunoglobulin preparations are the following (all values representing % w/w of the specific immunoglobulin on total immunoglobulin by weight, all values to be chosen so that the values for IgM, IgA, and IgG add up to 100%):

| IgM | IgA | IgG |
| --- | --- | --- |
| 10-40 | 10-35 | 25-80 |
| 17-35 | 15-30 | 30-73 |
| 18-28 | 15-27 | 48-66 |

The immunoglobulin preparation must be suitable for human administration, in particular it should fulfill applicable criteria of the European Pharmacopoeia Low Prekallikrein activator (≤35 IU/ml), e.g. as tested in accordance with the European Pharmacopoeia 8.8 of July 2016, published in January 2016 (title 2.6.15);

Low anti-complementary activity (≤1 $CH_{50}$/mg protein) e.g. as tested in accordance with the European Pharmacopoeia 8.8 of July 2016, published in January 2016 (title 2.6.17).

No viral activity

Preferably, the polymer content is equal or less than 7%, more preferably equal to or less than 5%. E.g. the molecular size distribution shows equal to or less than 7%, preferably equal to or less than 5%>1200 kDa (Ph. Eur. 0918).

The present invention has identified specific levels of two inflammatory markers, CRP and PCT, in order to stratify patients which benefit most from treatment with the IgM-enriched immunoglobulin preparation as defined herein. Both CRP and PCT are inflammatory markers and both are used in the diagnosis and monitoring of inflammation, bacterial infection, tissue injury, or sepsis. Despite their similarity as inflammatory markers, there are also some differences. CRP is a more common and fast routine marker in clinical practice, being included in many standard protocols of blood testing. In contrast, PCT is thought to differentiate bacterial infections from systemic inflammatory response of other causes with higher sensitivity and specificity compared with CRP (see e.g. Becze, Z., Molnar, Z., Fazakas, J., International Journal of Antimicrobial Agents 46 (2015) S13-S18).

The term "CRP" in the context of the present invention relates to C-reactive protein, a plasma protein belonging to the pentraxin family of proteins produced by the liver and by adipocytes. Clinically, CRP is known as a so-called "acute response" marker, which increases rapidly in response to tissue injury or inflammation. CRP can e.g. be measured using ELISA, immunoturbidimetry, nephelometry, rapid immunodiffusion, and visual agglutination. The CRP level according to the present invention should be measured using validated clinical laboratory methods. Such validated methods for clinical measurement of CRP are available to the person skilled in the art and routinely used in clinical practice. The CRP level according to the invention can be measured in blood, blood serum, or blood plasma, preferably in blood serum. Normal concentration of CRP in human serum is between 5 and 10 mg/L, increasing with age. Higher levels are found in late pregnant women, mild inflammation and subjects with viral infections (10-40 mg/L), active inflammation, or bacterial infection (40-200 mg/L). Interestingly, the inventors have found that a cut-off within the higher range of CRP values, which was previously not considered to be of particular diagnostic relevance, was highly predictive for a benefit from treatment with the immunoglobulin preparation according to the invention.

Therefore, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum CRP level of at least 50 mg/ml to at least 100 mg/l. Particularly, said patient has a serum CRP level of at least 70 mg/ml to at least 100 mg/l. More particularly, said patient has a serum CRP level of at least 70 mg/ml to at least 80 mg/l.

Also, the present invention relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum CRP-level of at least 50 mg/l, or at least 70 mg/l, or at least 75 mg/l, or least 80 mg/l, or least 100 mg/l.

The term "PCT" in the context of the present invention relates to procalcitonin, a precursor of the hormone calcitonin, PCT can be produced by several cell types and many organs in response to pro-inflammatory stimuli, in particular by bacterial products. Usually, the PCT level in the blood stream of healthy individuals is below 0.05 ng/ml. With the derangements that a severe infection with an associated systemic response brings, the blood levels of procalcitonin may rise to 100 ng/ml or more. In blood serum, procalcitonin has a half-life of 25 to 30 hours (30 to 45 hours in patients with severe renal dysfunction). Measurement of PCT has been used as a marker of severe sepsis and generally grades well with the degree of sepsis. Interestingly, the inventors have found that a PCT plasma level above certain cut-off values was highly predictive for a benefit from treatment with the immunoglobulin preparation according to the invention. PCT is generally stable in plasma and blood samples. The PCT level according to the invention can be measured e.g. in blood, blood serum, or blood plasma (preferably heparinized plasma or $K^+$-EDTA plasma), preferably blood serum. The PCT level according to the present invention can e.g. be measured using ELISA, immunoturbidimetry, nephelometry, rapid immunodiffusion, and visual agglutination. The PCT level according to the present invention should be measured using validated clinical laboratory methods. Such validated methods for clinical measurement of PCT are available to the person skilled in the art and routinely used in clinical practice.

In view of these findings, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum PCT level of at least 1.0 ng/ml to at least 15 ng/ml. Particularly, said patient has a serum PCT level of at least 1.0 ng/ml to at least 5.0 ng/ml Preferably, said patient has a serum PCT level of at least 1.0 ng/ml to at least 2.0 ng/ml.

Also, the present invention relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum PCT level of at least 1.0 ng/ml, or at least 1.5 ng/ml, or at least 2.0 ng/ml, or at least 5 ng/ml. Preferably, said patient has a serum PCT level of at least 1.5 ng/ml, or at least 2.0 ng/ml.

In the context of the present invention, it has also been found that a certain cut-off for the blood level of IgM in an sCAP patient was highly predictive for a benefit from treatment with the immunoglobulin preparation according to the invention. Validated methods for measurement of IgM are available to the person skilled in the art.

Therefore, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein the patient has a serum IgM level of equal to or lower than 0.4 g/l to equal to or lower than 1.5 g/l. Preferably, said patient has a serum IgM level of equal to or lower than 0.5 g/l to equal to or lower than 1.5 g/l. More preferably, said patient has a serum IgM level of equal to or lower than 0.5 g/l to equal to or lower than 1.0 g/l. More preferably, said patient has a serum IgM level of equal to or lower than 0.7 g/l to equal to or lower than 1.0 g/l.

Also, the present invention relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum IgM level of equal to or lower than 1.0 g/l, equal to or lower than 0.8 g/l, or equal to or lower than 0.7 g/l, equal to or lower than 0.6 g/l, or equal to or lower than 0.5 g/l.

In the context of the present invention, it has also been found that a certain cut-off for the blood level of IgG in an sCAP patient was highly predictive for a benefit from treatment with the immunoglobulin preparation according to the invention. Validated methods for measurement of IgG are available to the person skilled in the art.

Therefore, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein the patient has a serum IgG level of equal to or lower than 5 to equal to or lower than 10 g/l. Preferably, the patient has a serum IgG level of equal to or lower than 6 to equal to or lower than 10 g/l. More preferably, the patient has a serum IgG level of equal to or lower than 6 to equal to or lower than 8 g/l.

Also, the present invention relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum IgG level of equal to or lower than 9 g/l, or equal to or lower than 8 g/l, or equal to or lower than 7 g/l, or equal to or lower than 7 g/l, or equal to or lower than 6 g/l.

Figure 10:
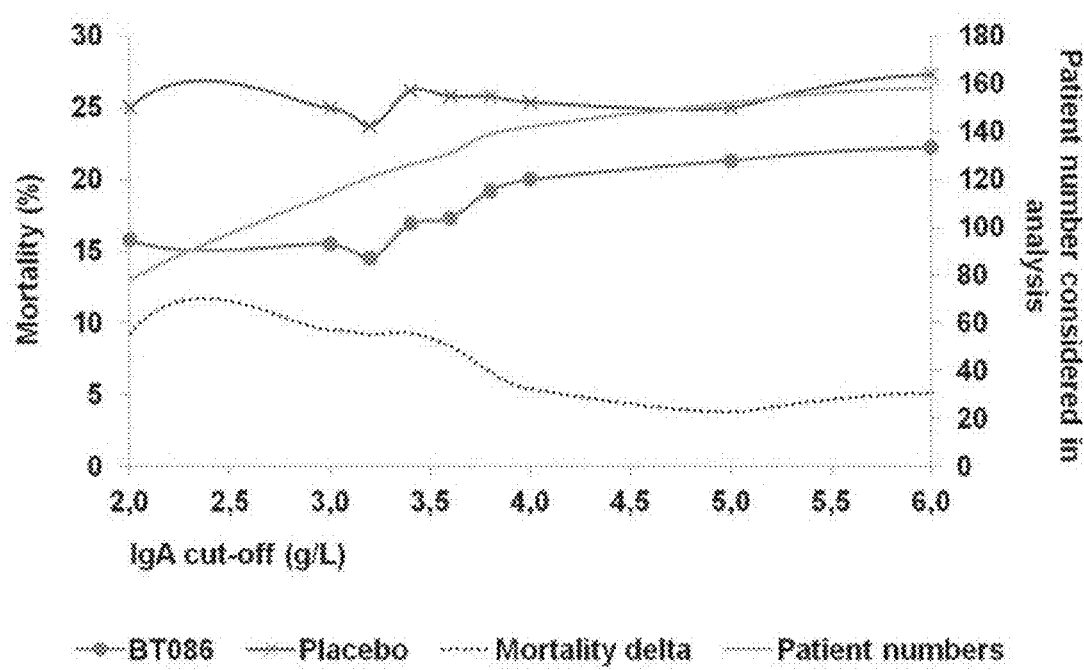
FIG. 10 shows mortality data for blood serum IgA cut-off levels against the difference in mortality (mortality delta, dotted line) between patients treated with the IgM-enriched immunoglobulin preparation as described herein (BT086) and patients treated with the placebo as described herein. Data are given for patients with IgA values equal or below the respective cut-off level. The levels were measured pre-dose, within 24 hours before treatment, almost all within 12 hours before start of treatment. Blood serum IgA cut-off levels plotted against the difference in mortality (mortality delta) between Ig-treated and placebo patients. In patients with IgA levels of equal to or below about 4 g/l IgA, the mortality delta of immunoglobulin-treated versus placebo-treated starts increasing. At a cut-off level of about 3 g/l IgA, a difference in mortality of 9.5% is observed, which further increases to more than 10% for lower cut-off values. Patient numbers (solid line) refers to the number of patients in the study which show values equal or above the respective cut-off level.

In the context of the present invention, it has also been found that a certain cut-off for the blood level of IgA in an sCAP patient was predictive for a benefit from treatment with the immunoglobulin preparation according to the invention, see FIG. 10. Validated methods for measurement of IgA are available to the person skilled in the art.

Therefore, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein the patient has a serum IgA level of equal to or lower than 2 g/l to equal to or lower than 4 g/l. Preferably, said patient has a serum IgA level of equal to or lower than 2 g/l to equal to or lower than 3.5 g/l. More preferably, said patient has a serum IgA level of equal to or lower than 2.5 g/l to equal to or lower than 3.5 g/l.

Also, the present invention relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient has a serum IgA level of equal to or lower than 4.0 g/l, equal to or lower than 3.5 g/l, or equal to or lower than 3 g/l, equal to or lower than 2.5 g/l, or equal to or lower than 2.0 g/l.

Any such level of PCT, CRP, IgM, IgG, or IgA as used in the context of the present invention should be present or measured at the time of sCAP diagnosis, at the time of admission to an Intensive Care Unit, or at the time of start of sCAP causal and/or supportive therapy. Said level of PCT, CRP, IgM, IgG, or IgA may also be present after sCAP diagnosis in a patient suffering from sCAP or undergoing treatment for sCAP. Particularly, such level should be present or measured at least once within 72 hours before to 72 hours after the start of vasopressor therapy or invasive mechanical ventilation. More particularly, such level should be present or measured at least once within 48 hours before to 48 hours after the start of vasopressor therapy or start of invasive mechanical ventilation. More particularly, such level should be present or measured at least once within 24 hours before to 24 hours after the start of vasopressor therapy or start of invasive mechanical ventilation. More particularly, such level should be present or measured at least once within 12 hours before to 12 hours after the start of vasopressor therapy or start of invasive mechanical ventilation. In the present context, start of vasopressor therapy means particularly start of systemic vasopressor therapy, more particularly start of sCAP-related vasopressor therapy.

Suitable assays for determining the immunoglobulin levels in serum or plasma, preferably in serum, are known to the skilled person. Possible methods include nephelometry or turbidimetry. Preferably, the IgM, IgG, and IgA levels mentioned refer to levels measured in blood serum using turbidimetry with Siemens Advia 2400 or Roche Hitachi Modular DPE, preferably with Siemens Advia 2400.

It has also been found in the context of the present invention that male patients benefit more from treatment with the IgM-enriched immunoglobulin preparation. It has also been found that patients not older than 65 years benefit more from treatment with the IgM-enriched immunoglobulin preparation.

Therefore, the present invention also relates to a human plasma-derived IgM-enriched immunoglobulin preparation, said immunoglobulin preparation not having been chemically modified and/or treated with beta-propiolactone, for use in adjunctive treatment of severe Community Acquired Pneumonia (sCAP) in a patient, wherein said patient is male and/or wherein said patient is not older than 65 years.

In light of the findings made in the context of the present invention, the invention also allows to identify or select patients who would benefit most or more from treatment with the IgM-enriched immunoglobulin preparation according to the invention. In particular, it has been found that patients with certain levels of CRP, PCT, IgM, IgG, and IgA benefit more from treatment than patients having other levels of said markers. For such patients, treatment with the IgM enriched immunoglobulin preparation according to the invention is generally useful and/or recommended. Therefore, the present invention also relates to a method of identifying or selecting an sCAP patient who would benefit from adjunctive treatment with a human plasma-derived IgM-enriched immunoglobulin preparation, said immunoglobulin preparation not having been chemically modified or treated with beta-propiolactone, comprising the steps of determining serum CRP level, and/or serum PCT level, and/or serum IgM level, and/or serum IgG level, and/or serum IgA level, or any combination thereof in a blood sample of the patient, wherein any one or more of: (1) a serum CRP level of at least 50 mg/l to at least 100 mg/l; (2) a serum PCT level of at least 1.0 ng/ml to at least 5.0 ng/ml; (3) a serum IgM level of equal to or lower than 0.5 g/l to at least 1.5 g/l; (4) a serum IgG level of equal to or lower than 5 g/l to at least 10 g/l; (5) a serum IgA level of equal to or lower than 2 g/l to equal to or lower than 3.5 g/l. More preferably, said patient has a serum IgA level of equal to or lower than 2.5 g/l to equal to or lower than 3.5 g/l, is indicative that the patient may or will benefit from such treatment. All other considerations in this specification can be applied mutatis mutandis to this method above.

Treatment with the IgM-enriched preparation may not be recommended for patients with selective, absolute IgA deficiency with known antibodies to IgA.

In an sCAP patient with one or more of the following conditions treatment with the IgM-enriched preparation may not be recommended or may require special caution, e.g. a reduced dosing or a particularly low infusion rate:

Patients on dialysis, chronic severe renal failure patients (CRCL<30 ml/min)
Patients with liver cirrhosis Child C
Decompensated cardiac failure
Pregnant or lactating women
Known relevant intolerance to immunoglobulins, vaccines or other substances of human origin
Patients with neutrophil count <1,000/mm$^3$ or platelet count <50,000/mm$^3$ Some lung diseases may interfere with sCAP causal or supportive therapy, such as cystic fibrosis, chronical infected bronchiectasis, tuberculosis, thoracal/head neck/hematologic malignancies.

Administration of the IgM-enriched immunoglobulin preparation may be less suitable in patients suffering from end-stage disease. Such are e.g. patients suffering from severe diseases impairing life expectancy (e.g. patients that are not expected to survive 28 days given their pre-existing uncorrectable medical condition). Such patients may have a life expectancy already too low to benefit from treatment with the IgM-enriched immunoglobulin composition as defined herein. The term "end-stage disease" is known to the skilled person. In the context of the present invention the term "end-stage disease" particularly relates to the last phase in the course of the progressive disease. More specifically, a patient having a life-expectancy of less than 28 days may be considered to have an end-stage disease.

The terms "treat" or "treatment" encompass both the therapeutic treatment of an already developed disease or condition, as well as prophylactic or preventative measures to avoid disease recurrence of pneumonia and/or to avoid secondary infections. Beneficial or desired clinical results due to said treatment may include, without limitation: curing of the disease, alleviation of one or more symptoms of the disease, diminishment of extent of disease, stabilized (i.e., not worsening) state of disease, delay or slowing of disease progression, prevention of disease recurrence, amelioration or palliation of the disease state, and the like. "Treatment" may also mean prolonging survival as compared to expected survival if not receiving treatment. Specifically, the term treatment as used herein aims to reduce 28-day mortality of the patient and to increase the number of ventilator free days (VFD) in the patient suffering from pneumonia or sCAP. Typical treatment of CAP or sCAP as used herein includes causal therapy aiming at removal of the cause of infection and supportive therapy aiming at providing life and/or organ support if needed. Causal therapy will typically include antibacterial or antiviral therapy to reduce or suppress the infectious agent(s) and accompanying toxin(s): However, due to antibiotic treatment sometimes additional toxins may be released. Treatment guidance can be obtained e.g. from Mandell et al., 2007 (IDSA/ATS Guidelines for CAP in Adults CID 44 (Suppl 2) S27). Antibiotic therapy may include e.g. Ceftriaxone, Ciprofloxacin, Clarithromycin, Erythromycin, Levofloxacin, Pip/Tazo, Vancomycin, Meropenem, The antibiotics may optionally be combined with macrolides, respiratory quinolones, doxicycline, etc. (Mandell et al., 2003 Dec. 1; 37(11):1405-33; Niederman et al., 2001 Am J Respir Crit Care Med. June; 163(7):1730-54).

VFDs are defined as the number of days between successful extubation (weaning) from mechanical ventilation and day 28 after enrollment of the patient into the study. The VFD is "0" if the patient dies before end of follow up (28 days), even after successful weaning. Therefore, VFDs combine mortality and duration of ventilation in survivors (Schoenfeld et al. 2002 Crit Care Med 30(8):1772-1777 (2002)).

Supportive therapy may typically include respiratory aid and/or oxygen administration, in particular through mechanical ventilation such as invasive mechanical ventilation, and/or treatment with vasopressors. Other intensive care measures may be support of the vital organ functions as deemed appropriate, e.g. renal support. The immunoglobulin preparation as described herein is intended to be used as an adjunctive treatment, i.e. in combination with any causal and/or supportive therapy.

The terms "sCAP therapy" or "sCAP treatment" hence encompass the causal and/or supportive therapies used in a clinical or health-care setting and exemplified herein. The IgM enriched immunoglobulin preparation as used in the context of the present invention may be administered in an therapeutically effective amount or a prophylactically effective amount. The term "prophylactically effective amount" refers to an amount of the pharmaceutical composition that inhibits or delays in a subject the onset of pneumonia, or sCAP in a subject. The term "therapeutically effective amount" as used herein, refers to an amount of pharmaceutical composition that elicits the biological or medicinal response in a subject that is being sought by a medical doctor or clinician, which may include inter alia alleviation of the symptoms of the disease or amelioration of the disease or condition being treated. Methods are known in the art for determining therapeutically and prophylactically effective doses for the pharmaceutical compositions defined herein.

The present invention includes an IgM-enriched immunoglobulin preparation for use as an adjunctive treatment to the above referenced causal and supportive sCAP therapies, particularly in addition to antibiotic treatment and/or treatment with vasopressors and/or treatment with invasive mechanical ventilation.

The term "adjunctive treatment" of sCAP is understood by the skilled person. In particular, the term "adjunctive treatment" includes treatment with the IgM-enriched immunoglobulin preparation according to the invention in parallel, subsequently to, before or overlapping with said causal and/or supportive therapy, such as a treatment with one or more antibacterial, antifungal or antiviral agents, and/or respiratory and organ function support. More preferably, adjunctive treatment means that the treatment with the IgM-enriched immunoglobulin preparation is commenced early after, preferably shortly after sCAP diagnosis, e.g. within 24 hours before or after sCAP diagnosis, preferably within 1 to 24 hours after start of vasopressor therapy and/or start of invasive mechanical ventilation, or as explained in more detail and elaborated further elsewhere in this specification. Adjunctive treatment with the IgM-enriched immunoglobulin preparation may also be commenced within up to about 24, 48, or 72 hours after sCAP diagnosis in a patient suffering from sCAP, if said patient then develops a serum CRP level and/or a serum PCT level and/or a serum IgM level and/or a serum IgG level and/or a serum IgA level as specified elsewhere in this specification. In light of these considerations, the present invention also relates to a human plasma-derived IgM-enriched immunoglobulin preparation, said immunoglobulin preparation not having been chemically modified and/or treated with beta-propiolactone, for use in treatment of severe Community Acquired Pneumonia (sCAP) in a patient undergoing treatment with an antibiotic agent and/or a vasopressor and/or invasive mechanical ventilation, wherein said patient has a serum CRP level and/or a serum PCT level and/or an serum IgM level and/or an serum IgG level and/or a serum IgA level as specified elsewhere in this specification.

The term "invasive mechanical ventilation" or "mechanical invasive ventilation" is well understood by the person skilled in the art. Mechanical ventilation is a method to mechanically assist or replace spontaneous breathing of a patient, e.g. using a medical ventilator (also known as respirator). A medical ventilator (or simply ventilator in context of the present invention) is a machine designed to mechanically move air or another suitable gas mix into and/or out of the lungs, to assist or replace the mechanism of breathing for a patient who is physically unable to breathe, or breathing insufficiently. There are two main modes: positive pressure ventilation, where air (or another gas mix) is pushed into the lungs, and negative pressure ventilation, where air is, in essence, sucked into the lungs. Mechanical ventilation is called invasive, if it involves any instrument penetrating through the mouth (e.g. an endotracheal tube) or the skin (such as a tracheostomy tube). In particular, in the context of the present invention, "invasive mechanical ventilation" relates to endotracheal ventilation and ventilation by tracheostomy, more particularly to endotracheal ventilation.

It is expected that patients benefit more from the IgM-enriched immunoglobulin preparation if it is administered early at the time of sCAP diagnosis or even before sCAP diagnosis. Therefore, the present invention also relates to a human plasma-derived IgM-enriched immunoglobulin preparation, said immunoglobulin preparation not having been chemically modified and/or treated with beta-propiolactone, for use in prophylaxis and/or treatment of severe Community Acquired Pneumonia (sCAP), particularly in a patient expected to develop sCAP, wherein said patient has a serum CRP level and/or a serum PCT level and/or an serum IgM level and/or an serum IgG level and/or a serum IgA level as specified elsewhere in this specification. Preferably, such prophylaxis or treatment or is adjunctive to antibiotic therapy. Particularly, said patient is already suffering from Community Acquired Pneumonia (CAP). In the present context, "a patient expected to develop sCAP" means that said patient is expected to fulfil the criteria of sCAP as defined herein elsewhere within 72 hours, more preferably within 48 hours, more preferably within 24 hours, more preferably within 12 hours, particularly if the patient is not responding or responding poorly to antibiotic therapy. Treatment with the IgM-enriched immunoglobulin preparation according to the invention may then be started before diagnosis of sCAP.

The IgM-enriched immunoglobulin preparation as defined herein may be administered as deemed appropriate by the person skilled in the art. However, the inventors consider that early treatment with the IgM-enriched immunoglobulin preparation after sCAP diagnosis or start of sCAP therapy would improve the benefit to the patient, e.g. by early opsonisation of the pathogen or early neutralization of toxins.

Therefore, for example, the preparation may be administered in 3 to 10 daily doses or infusions over 21 days or three weeks after sCAP diagnosis, or admission to the Intensive Care Unit, or start of vasopressor therapy or start of invasive mechanical ventilation. Preferably, the at least three daily doses, more preferably at least four or five daily doses, are administered immediately consecutive to sCAP diagnosis, admission to the Intensive Care Unit, or start of vasopressor therapy or start of invasive mechanical ventilation. Preferably, the first daily dose is administered within 24 hours, more preferably between 1 and 12 hours after start of sCAP causal or supportive therapy. More particularly, the first daily dose is administered within 24 hours, more preferably between 1 and 12 hours after admission to the Intensive Care Unit. Even more particularly the first daily dose is administered within 24 hours, more preferably between 1 and 12 hours after start of vasopressor therapy and/or start of invasive mechanical ventilation. In the present context, start of vasopressor therapy means particularly start of systemic vasopressor therapy, more particularly start of sCAP-related vasopressor therapy. In the present context, admission to an Intensive Care Unit means particularly sCAP-related admission to an Intensive Care Unit. Administration "within 24 hours", or "between 1 and 12 hours" particularly means that the administration is preferably started within this time frame. The skilled person will understand that the time e.g. for the infusion of the entire initial or first daily dose may extend beyond this time-frame.

In the context of starting treatment with the IgM-enriched immunoglobulin preparation, "after start of vasopressor therapy and/or start of invasive mechanical ventilation" means that either the start of vasopressor therapy or the start of invasive mechanical ventilation is sufficient to trigger start of treatment according to the time-windows mentioned herein. If both vasopressor therapy and invasive mechanical ventilation are initiated, then the start of treatment is triggered by the earlier of both.

In another treatment regimen, the IgM-enriched immunoglobulin preparation may be administered according to the following treatment regimen: a first daily dose to be administered within 24 hours, preferably between 1 and 12 hours after start of vasopressor therapy and/or start of invasive mechanical ventilation, followed by 3 to 10, preferably 3 to 6, more preferably 5, consecutive daily doses, and optionally one or more maintenance doses at 10 to 18 days, more preferably 12 to 16 days, more preferably 14 days, after the first administration of said immunoglobulin preparation.

In a more specific preferred example, the treatment regimen for use with the immunoglobulin preparation as defined herein as an adjunctive therapy can comprise a first daily dose within 1 and 24 hours, more particularly within 1 and 12 hours after sCAP diagnosis and/or admission to the Intensive Care Unit and/or start of vasopressor therapy or start of invasive mechanical ventilation, more particularly within 1 to 12 hours after start of start of invasive mechanical ventilation, followed by daily doses for 4 consecutive days.

In the context of administration regimens, start of vasopressor therapy means particularly start of systemic vasopressor therapy, more particularly start of sCAP-related vasopressor therapy. In the present context of administration, admission to an Intensive Care Unit means particularly sCAP-related admission to an Intensive Care Unit.

The daily dosage of the immunoglobulin treatment is calculated based on the IgM protein weight administered to the patient per kg bodyweight. Preferably, the doses are based on the weight at hospital admission, prior to treatment. A dosage of e.g. 42 mg IgM/kg bodyweight indicates that per kilogram bodyweight of the patient upon admission to the hospital or upon start of treatment, 42 mg of IgM protein is to be administered to said patient. Given that the immunoglobulin preparation as a whole comprises also other proteins, mainly IgG and IgA proteins, this implies that the amount of preparation to be administered will be higher and is preferably calculated on the mean concentration of IgM in the preparation. For example, if the IgM concentration in the total protein preparation is 23%, a dose of 42 mg IgM/kg bodyweight would be achieved by administering about 182.7 mg of the total immunoglobulin preparation per kg The assay(s) used for determining the immunoglobulin levels in the patient undergoing treatment can be selected according to the knowledge of the skilled person. One possible method is nephelometry on a blood sample of the patient in accordance with the European Pharmacopoeia.

In exemplary embodiments, the treatment schemes can be as follows:

|  | Day 1* | Day 2 | Day 3 | Day 4 | Day 10-18 |
|---|---|---|---|---|---|
| 4 daily doses | 40-45 mg IgM/kg | 40-45 mg IgM/kg | 40-45 mg IgM/kg | 40-45 mg IgM/kg |  |
| 4 daily doses plus maintenance dose | 40-45 mg IgM/kg | 40-45 mg IgM/kg | 40-45 mg IgM/kg | 40-45 mg IgM/kg | 40-45 mg IgM/kg or 60-65 mg IgM/kg |
| Loading dose plus 3 daily doses | 60-65 mg IgM/kg | 40-45 mg IgM/kg | 40-45 mg IgM/kg | 40-45 mg IgM/kg |  |
| Loading dose plus 3 daily doses and maintenance dose | 60-65 mg IgM/kg | 40-45 mg IgM/kg | 40-45 mg IgM/kg | 40-45 mg IgM/kg | 40-45 mg IgM/kg or 60-65 mg IgM/kg |

*Day 1 indicates the first day of sCAP treatment, i.e. the first dose of the IgM-enriched preparation is typically administered between 1 and 24, preferably between 1 and 12 hours after start of sCAP treatment with vasopressors or start of invasive mechanical ventilation.

bodyweight. In analogy, if another mean percentage of IgM would be used in the preparation, the amount of immunoglobulin preparation to be administered can be easily calculated by the skilled person.

The skilled person is able to define an effective amount of the IgM-enriched immunoglobulin preparation. Preferably, each daily immunoglobulin administration as defined herein is dosed in a daily dose of between 30 and 80 mg IgM/kg bodyweight of the patient, preferably of between 35 and 65 mg IgM/kg bodyweight, more preferably of from 40 to 45 mg IgM/kg bodyweight or from 60 to 65 mg IgM/kg bodyweight, or a dose equivalent thereto. Also lower doses such as 20 mg IgM/kg bodyweight may be envisaged, for example if the patient has a serum IgM level of above 1.5 g/l or 2 g/l at the beginning of treatment, or if the patient is suffering from a renal disorder, renal insufficiency, or a hepatic disorder.

The first daily administration may comprise a loading dose which can be higher than the subsequent daily doses, such as to create a loading effect of the immunoglobulins in the patient. Typical doses of such a loading dose may be 1.5 to 2 times the amount of the subsequent daily doses. For example, if the normal daily dose administered is 40 to 45 mg IgM/kg bodyweight, then a suitable loading dose may comprise between about 60 to about 80 mg IgM/kg bodyweight. In some embodiments, the initial daily dose administered is between 50 and 80 mg IgM/kg bodyweight, preferably between 60 and 65 mg/kg bodyweight. Such a loading dose can e.g. be administered by increasing the duration of infusion.

In some embodiments, the treatment scheme can also include the administration of a maintenance dose, a certain period of time after the daily doses have been administered. Typically, such a maintenance dose would be administered on any one of days 10 to 16 after the administration of first dose or loading dose. Such a maintenance dose can be similar to the other doses such as between 40 and 80 mg IgM/kg bodyweight, preferably of between 40 and 65 mg IgM/kg bodyweight, more preferably of from 40 to 45 mg IgM/kg bodyweight or from 60 to 65 mg IgM/kg bodyweight and/or can be tailored to the patient's response or needs, e.g. based on the IgM level measured in a sample of the patient during treatment. The maintenance dose could hence for example be administered at a time where the blood plasma level of IgM drops below the level of 1.0 g/l, preferably 0.7 g/l, more preferably 0.5 g/l.

The immunoglobulin preparation or pharmaceutical composition as defined herein can be administered particularly via intravenous infusion. Preferably said infusion is done using a separate infusion line to avoid mixing with other drugs or medications that could interfere with the immunoglobulin preparation. Infusion rates can be chosen by the skilled person. Preferably, the infusion rate is lower than or equal to about 8 mg IgM/min., preferably lower than or equal to about 6 mg IgM/min. Preferably, the initial infusion rate for a given patient is lower than or equal to about 2, preferably 1.5, more preferably equal to or less than 1.2 mg IgM/min. This corresponds to an infusion rate of lower than or equal to about 0.7 ml/min, preferably equal to or less than about 0.5 ml/min. and an initial infusion rate of less than about 0.1 ml/min in the case of immunoglobulin preparation comprising 5% (w/v) total immunoglobulin and about 23% (w/w) IgM of the total immunoglobulin. A low initial infusion rate allows time to check whether the patient shows an undesired reaction to the immunoglobulin preparation as defined herein. More preferably, the initial infusion rate of about 0.1 ml/min (1.15 mg IgM/min.) may be increased about every 10 min to a target infusion rate of about 0.5 ml/min (5.75 mg IgM/min). Said infusion can typically be done by "continuous infusion" meaning the infusion is maintained at approximately the prescribed rate without substantial interruption for most of the prescribed duration. The skilled person will understand that the infusion may e.g. be interrupted for short times for change of containers comprising the preparation or composition. Also intermittent intravenous infusion can be used, as long as the total daily dose remains the same as for the continuous infusion. The total daily dose may also be stretched over 24 hours, resulting in a continuous infusion of the daily doses. The term "without substantial interruption" allows e.g. for interruptions of the infusion in order to change an empty container comprising the immunoglobulin preparation or in order to allow for intermittent infusion of another medication. For both types of infusion, the recommended daily dose as described herein should be respected.

The dose administered of the immunoglobulin preparation or pharmaceutical composition comprising the latter can also further be adjusted according to immunoglobulin levels in the patient after administration. Preferably said levels are measured at a suitable time after administration, e.g. before the intended next administration.

The inventors have also realized that the IgM levels in blood increase build up over several days after consecutive daily administrations of the immunoglobulin preparation of the invention. In addition, it was found that patients with low initial levels of IgM benefit particularly well from treatment. On the other hand, patients with particularly low initial levels of IgM may have been underdosed. Based on these findings, the inventors have developed an adapted administration scheme involving a loading dose. Therefore, preferably, the first dose of the immunoglobulin preparation according to the invention is administered in a dose higher than the normal daily dose, such as to create a loading effect of the immunoglobulins in the subject. Typical doses of such a loading dose would be about 1.5 or 2 times the consecutive daily dose(s). It was found that such loading dose could increase the IgM level in the patient early after start of treatment, but would not affect much the maximal IgM level in the patient after administration of the subsequent doses. Preferably such loading dose can be administered by extending the infusion time.

Such loading dose may also be made dependent on the initial IgM level of the patient, since the data shows that patients having a lower IgM level at the start of the treatment tend to benefit stronger from IgM administration than other patients. A loading dose would more rapidly bring the IgM levels of the patients back to normal levels. Again nephelometry can be used to measure the IgM level of said patient.

Figure 5A:
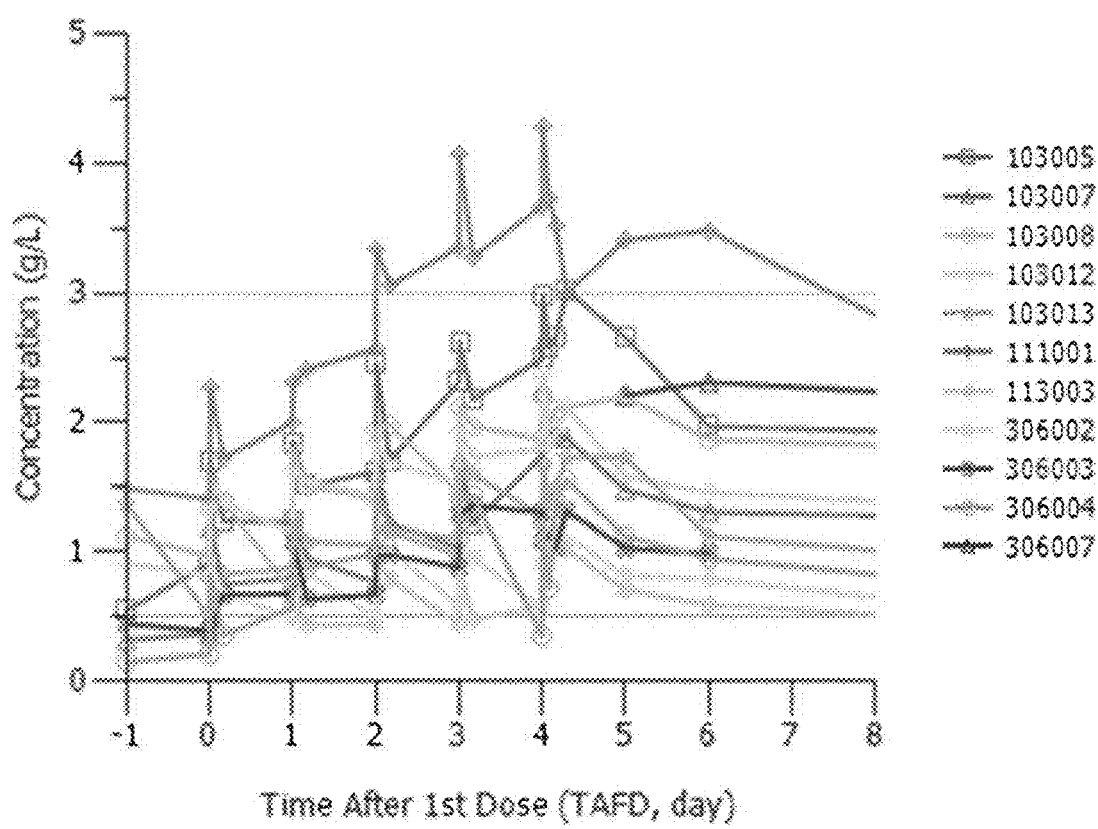
FIG. 5A shows IgM levels obtained in sCAP patients treated with the IgM-enriched immunoglobulin preparation (BT086) as described herein. Each line represents the data of one patient.
Figure 5B:
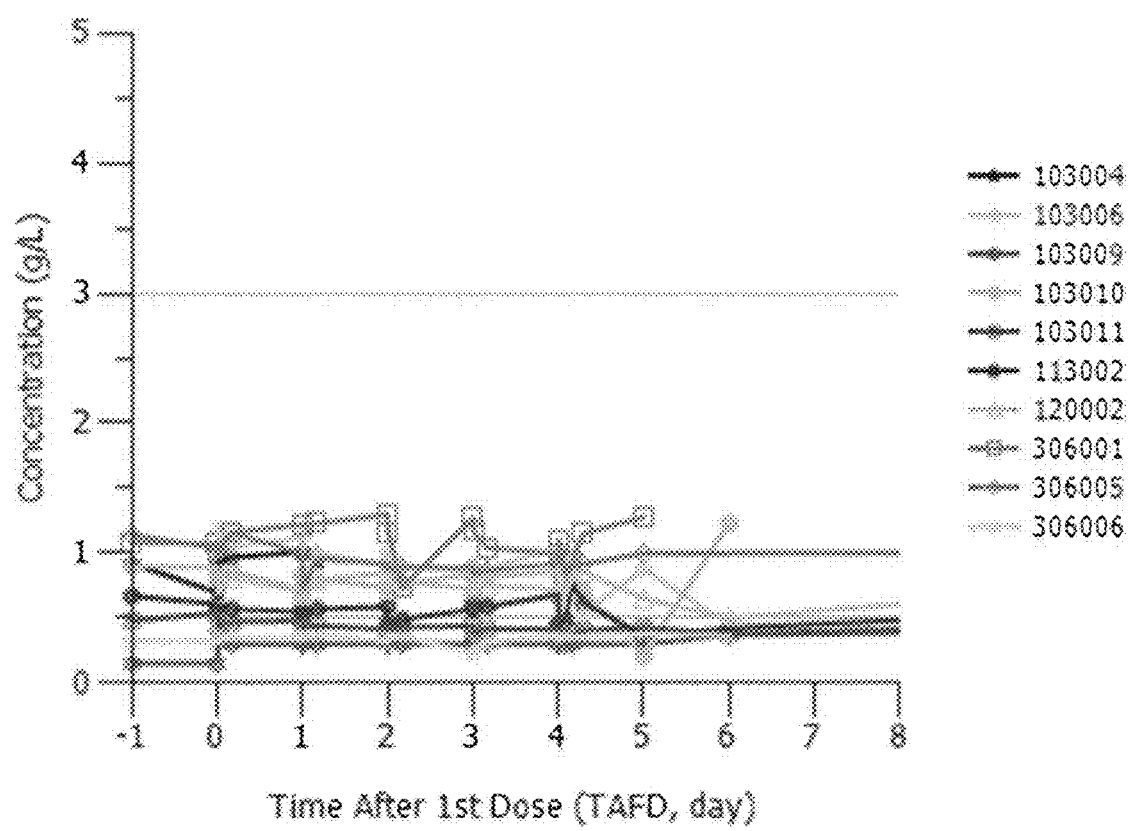
FIG. 5B shows IgM levels obtained in sCAP patients treated with placebo. Each line represents the data of one patient.

In the context of the present invention, the inventors have also realized (cf. FIG. 5A) that the IgM levels decrease already significantly in the 5 day period after treatment with the IgM-enriched immunoglobulin preparation as defined herein has ended. In addition, patients may enter into an immunocompromised state during the later course of the disease, as it has been discussed for sepsis patients in general. Thus, patients can be at risk of re-emergence of the infection and/or at risk of secondary infections. As the human immunoglobulin preparation comprises antibodies against a broad range of pathogens, patients may benefit from one or more additional maintenance doses.

Based on these findings and considerations, the inventors have developed an adapted administration scheme involving a maintenance dose. In some embodiments, the treatment scheme hence can also include the administration of a maintenance dose, a certain period of time after the daily doses have been administered. Typically, such a maintenance dose would be administered on any one of days 10 to 18 after the initial dose, preferably any one of days 12 to 16 after the initial dose has been administered. Such a maintenance dose can be similar to the other doses such as between 30 and 80 mg IgM/kg bodyweight, preferably of between 35 and 70 mg IgM/kg bodyweight, more preferably of from 40 to 45 mg IgM/kg bodyweight or from 60 to 65 mg IgM/kg bodyweight and/or can be tailored to the patient's response or needs, e.g. based on the IgM level measured in a sample of the patient during treatment. The maintenance dose could hence for example be administered at a time where the blood plasma level of IgM drops below the normal level of 0.5 g/l. Such maintenance dose administration may be repeated, if necessary.

sCAP is a severe disease and patients may develop further complications during treatment. Therefore treatment may be adapted to the condition of the patient. For example, the treatment may be interrupted or the dose may be reduced if the patient develops renal failure during treatment and/or if the patient develops a severe hemolysis during treatment.

The treatment with the IgM-enriched immunoglobulin preparation is preferably started within 1 to 24, more preferably within 1 to 12 hours from start of sCAP causal or supportive therapy, in particular of start of treatment with e.g. vasopressors and/or start of invasive mechanical ventilation.

The term "vasopressor" is known to the skilled person and indicates an anti-hypotensive agent, i.e. any agent that aims at raising a reduced blood pressure. Exemplary vasopressors are vasoconstrictors increasing the total peripheral resistance, agents sensitizing adrenoreceptors for catecholamines such as glucocorticoids, and agents increasing cardiac output such as catecholamines. Preferred vasopressors in the context of the present invention include catecholamines, particularly dobutamine, epinephrine, dopamine, and norepinephrine.

The human IgM-enriched immunoglobulin preparation as defined herein can e.g. be produced according to the method disclosed in International patent applications WO2011/131786 and WO2011/131787 (Biotest) herein incorporated in its entirety by reference. In summary, the method comprises the steps of collecting or obtaining blood plasma from blood donors, and purifying the immunoglobulins from said plasma pool using Cohn plasma fractionation methods or modifications and further purification steps. Using said methods, the immunoglobulin containing product is isolated which comprises 90%, preferably at least 93%, more preferably at least 95% pure immunoglobulin based on the total protein content (e.g. from a Cohn Fraction III or I/III).

The pooled human plasma used for obtaining the IgM preparation is preferably negative for HCV-RNA, HBV-DNA, HAV-RNA, and HIV-RNA; and Parvo B19 DNA levels preferably do not exceed $1 \times 10^4$ IU/mL.

The above process may comprise additional steps which are in the routine of the skilled person, such as e.g. precipitation steps, chromatography steps and or filtration or centrifugation steps. The conditions of each step such as particular pH values or salt concentrations can be determined by the skilled person. Further guidance and preferred conditions can be found e.g. in WO2011/131786 (Biotest) herein incorporated in its entirety by reference.

As mentioned elsewhere, the process should contain no step of chemical modification or beta-propiolactone treatment of the immunoglobulin preparation or any intermediate of the immunoglobulin preparation.

For example, in brief, the process for manufacturing the IgM-enriched immunoglobulin preparation may comprise the following steps:

(a) preparing from human plasma a plasma fraction as a solution containing immunoglobulins
(b) mixing a $C_7$ to $C_8$ carboxylic acid, e.g. octanoic acid, with the solution and treating the mixed solution with a vibrating agitator (e.g. Graber & Pfenninger GmbH) to precipitate contaminating proteins;
(c) separating the precipitated proteins from the solution to yield the IgM containing immunoglobulin composition
(d) incubating the IgM containing immunoglobulin composition at between pH 3.5 and pH 4.5 to form an incubated solution
(e) irradiating the incubated solution with UVC to form an UVC irradiated solution; and
(f) filtering the UVC irradiated solution under sterile conditions to form the immunoglobulin preparation suitable for intravenous administration in humans.

As indicated above, the immunoglobulin preparation as defined herein can be formulated into a suitable pharmaceutical composition, preferably into a solution suitable for intravenous infusion. In this respect, the immunoglobulin preparation as defined herein can be a composition, preferably a pharmaceutical composition, more preferably a (pharmaceutical) composition suitable for intravenous infusion.

The immunoglobulin preparation according to the present invention can be formulated into a pharmaceutical composition. Preferably, the pharmaceutical composition according to the present invention comprises between about 20, preferably about 30, more preferably about 40 and about 100 gram immunoglobulin protein per liter solution, e.g. about 45 to 55 g/l. The composition may comprise suitable excipients, such as 0.2 to 0.5 M glycine. Preferably, the formulation is buffered at a pH of 4 to 7, preferably a pH of 4.3 to 4.7 in order to maintain a good stability of the product at 2 to 8° C.

The pharmaceutical composition may additionally include or may be combined with other active substances suitable for treatment of pneumonia or for treating sepsis such as: suitable antivirals, anti-inflammatories, or immune modulators, suitable antibiotics, antifungal agents, respiratory aid such as oxygen or mechanical ventilation, fluid resuscitation and organ function replacement such as renal replacement therapy.

The pharmaceutical compositions may further comprise pharmaceutically acceptable additives, excipients, or other substances which allow for more effective administration.

The immunoglobulin preparation as defined herein can be formulated in any suitable pharmaceutical form, with a pharmaceutical excipient, or in a pharmaceutical solution or formulation, preferably in a solution for intravenous infusion.

A pharmaceutical composition comprising the IgM-enriched immunoglobulin preparation may e.g. be formulated as a liquid solution for infusion. Such composition may e.g. comprise ≥90%, preferably ≥95% Immunoglobulins comprising 18-28% IgM; 15-27% IgA; and 48-66% IgG by weight of total immunoglobulin, in 0.3 M glycine, at a pH of between 4.3-4.7.

Preferably, the IgM-enriched preparation is in a form or composition which is stable in liquid form for at least 3 months, preferably at least 6 months and most preferably at least two years at 2 to 8° C., which means that there is no fragmentation or polymerization of IgM above 7%, preferably 5%, measured in HPSEC, no increase of proteolytic activity, no decrease of IgM antibody activity against *Escherichia coli* and IgM antibody activity against Pneumococcus saccharide of more than 25% and no increase in anti-complementary activity of more than 25%, staying below 1 CH50/mg protein. Still further, the IgM-enriched preparation is in a form or composition which is stable in liquid form for at least 3 months, preferably at least 6 months, and most preferably at least one year at room temperature (between 23 and 27° C.) as assessed by the same criteria.

The (pharmaceutical) composition comprising the immunoglobulin preparation can also be filled into a suitable container under sterile conditions. A suitable container can be a flask or a bottle suitable for infusion, e.g. comprising a sealed pierceable rubber stopper. Therefore, the present invention also relates to a container such as a flask or a bottle comprising the pharmaceutical composition comprising the immunoglobulin preparation as defined herein. Said flask or bottle may e.g. comprise about 50 ml to about 100 ml of an about 5% or about 10% total immunoglobulin preparation according to the invention, preferably comprising 10 to 40%, preferably 18 to 28% IgM by weight of the total immunoglobulin. In addition, the present invention also relates to a package or kit comprising single or multiple containers, flasks or bottles comprising the pharmaceutical composition alongside with instructions for administration (preferably with instructions for administration according to the administration scheme of the present invention).

The respective aspects of the invention as described herein will now be further illustrated by the following non-limiting examples.

All references cited herein are hereby incorporated by reference in their entirety.

EXAMPLES

Example 1

Preparation of the Human Immunoglobulin Preparation According to the Present Invention The human immunoglobulin preparation as defined herein can be prepared using the general process as disclosed in WO2011/131786. In summary the following steps were used: Plasma was obtained from healthy donors, pooled and an initial purification of human IgM is carried out by classical Cohn plasma fractionation methods or known modifications thereof (e.g. Cohn/Oncley, Kistler/Nitschmann). Using cold ethanol precipitation processes the IgM fraction is recovered in Cohn fraction III or fraction I/III. The preparation was at least 95% pure immunoglobulin based on the total protein content. The product was not treated with beta-propiolactone and not pasteurized. It was manufactured with following steps: Mixing octanoic acid with the solution and treating the mixed solution with a vibrating agitator (Graber & Pfenninger) to precipitate contaminating proteins; the precipitated proteins were separated from the solution to yield the IgM containing immunoglobulin composition. The IgM containing immunoglobulin composition was incubated at between pH 3.5 and pH 4.5 to form an incubated solution. The incubated solution was treated with UVC to form an UVC irradiated solution; and the UVC irradiated solution was filtered under sterile conditions to form the immunoglobulin preparation suitable for intravenous administration in humans.

The final product had the following characteristics:

| Formulated Bulk | Analytical Method | Average values for immunoglobulin lots |
| --- | --- | --- |
| Total protein | Biuret | 45-55 g/l |
| Total % immunoglobulins on total protein | Nephelometry | >=95% |
| Total % IgG on total protein | Nephelometry | 48-66% |
| Total % IgA on total protein | Nephelometry | 15-27% |
| Total % IgM on total protein | Nephelometry | 18-28% |

The IgM enriched immunoglobulin preparation was stable for at least 24 months at +2° C. to +8° C.

The IgM enriched immunoglobulin preparation was also shown to have the following characteristics:

Low Prekallikrein activator (≤35 IU/ml),

Low IgM polymer content (≤5%), and

Low anti-complementary activity (≤1 $CH_{50}$/mg protein), as tested in accordance with the European Pharmacopoeia 8.8 of July 2016, published in January 2016 (title 2.6.17).

The IgM-enriched immunoglobulin preparation was also tested for titer against pathogens: The preparation comprised antibodies to streptolysine-O antigen (IgG) 200 IU/ml) Also titers of the antibody activities can be measured.

The product is designated BT086 or BT0588

Example 2

Clinical Trial Results of an IgM Enriched Immunoglobulin Preparation (BT-086) Used as Adjunctive Treatment for sCAP A randomized, double-blind, placebo-controlled phase II trial was performed in 160 hospitalized and patients with severe community acquired pneumonia (sCAP) ventilated by invasive mechanical ventilation, using the human immunoglobulin preparation as prepared and formulated in Example 1, to evaluate the efficacy, safety and pharmacokinetics thereof.

Placebo

The placebo used as a control in the study was a 1% Human albumin solution for infusion. Human albumin was chosen as the placebo as it has a similar appearance to BT086, thereby maintaining blinding. The placebo had the following composition:

Human plasma proteins: 10 mg/mL, of which Albumin 96%
Caprylate (stabiliser): 0.5-2.0 mmol
N-Acetyl-DL-tryptophanate (stabiliser): 0.5-2.0 mmol)
Sodium: 140-160 mmol)
pH: 6.7-7.3

The commercial human albumin 20% drug product Albiomin from Biotest was used as starting material for manufacturing of 1% Human albumin placebo.

Patient Characteristics

In this section an overview is given of the patient's characteristics. The main characteristics are given in the table below:

| Patient demography | | |
|---|---|---|
| | Placebo | IgM-enriched preparation |
| Patients enrolled | 79 | 81 |
| Male | 57 | 56 |
| Female | 22 | 25 |
| Age (mean/median) | 65.5/67 | 63.7/66 |
| PCT ng/ml (day −1) (mean/median) | 22.6/7.2 | 8.2/2.3* |
| CRP mg/l (day −1) (mean/median) | 276/233 | 220/217 |
| APACHE II (mean/median) | 26.2/25 | 23.1/23 |
| SOFA at study day 1 (mean/median) | 115./11.0 | 10.6/11.0 |

*the difference in PCT level is due to the presence of a limited number of aberrant samples.

Patient Inclusion Criteria:

In general the patients needed to comply with one or more of the following criteria in order to be selected for the clinical trial:

Written informed consent obtained prior to any study-specific assessments

Major sCAP criterion: Need for endotracheal ventilation Patient receiving adequate antibiotic treatment for pneumonia Prior to invasive mechanical ventilation and therapy, the patient must have at least one of the following two signs of inflammation: Fever/Hypothermia or White Blood Cell (WBC) count >10.000/mm$^3$ or WBC <4.500/mm$^3$.

Patient must have at least one of the following signs and symptoms of pneumonia: new or increased cough; production of purulent sputum or change in sputum characteristics; dyspnea or tachypnea (respiratory rate >20 breaths/minute); pleuritic chest pain; auscultatory findings on pulmonary examination of rales and/or crackles and/or evidence of pulmonary consolidation (e.g. dullness on percussion, bronchial breath sounds, or egophony).

Radiological (or other imaging technique) evidence of (an) infiltrate(s) consistent with bacterial pneumonia Pneumonia has been acquired outside the hospital. In hospital admitted patients, pneumonia has been diagnosed a maximum of 72 hours after admission. Patients from nursing homes or similar institutions are eligible Treatment of patient with BT086 must start within 12 hours but not earlier than 1 hour after start of invasive mechanical ventilation Need for endotracheal ventilation means that also patients with ventilation by tracheostomy were included.

Patient Exclusion Criteria:

Patients were excluded from the clinical trial in case they complied with the following criteria:

Patients with suspected hospital-acquired pneumonia

Presence of other severe diseases impairing life expectancy (e.g. patients are not expected to survive 28 days given their pre-existing uncorrectable medical condition).

Selective, absolute IgA deficiency with known antibodies to IgA

Patients with neutrophil count <1.000/mm$^3$ or platelet count <50.000/mm$^3$

Dose Calculation and Administration

All doses were based on the recorded hospital admission weight, prior to treatment. The calculated total dose for all infusions was based on the admission weight, and was recorded for each dose.

A solution comprising the immunoglobulin preparation was infused intravenously via an infusion pump using a separate infusion line. Care was taken not to mix with other drugs or medications. Based on compatibility experience with other immunoglobulin preparations, immunoglobulin preparation was infused sequentially into an IV line containing either 0.9% sodium chloride or 5% dextrose saline. The amount of immunoglobulin preparation administered per day depends on the bodyweight of the patient. In order to reach a dose of 42 mg IgM/kg bodyweight in e.g. a subject of 70 kg: 70×3.65 ml of the immunoglobulin preparation=255.65 ml is infused daily, at a maximum infusion rate of 0.5 ml/min (duration=8:30 h). Fora patient of 100 kg, 365.22 ml of solution should be administered (duration=12:10 h).

Dosage Regimen

The dosing regimen of the adjunctive therapy was as follows: Five infusions of the IgM enriched preparation (BT086) of 42 mg IgM/kg bodyweight over 5 consecutive days, starting with a first dose in a period of between 1 and 12 hours after invasive mechanical ventilation.

The following treatment scheme was typically applied:

| | Dose Timing | Doses | Dose # |
|---|---|---|---|
| Daily | Day 1 (1 to 12 h after start of invasive mechanical ventilation) | 42 mg IgM/kg bodyweight | 1 |
| | Day 2 | 42 mg IgM/kg bodyweight | 2 |

| Dose Timing | Doses | Dose # |
|---|---|---|
| Day 3 | 42 mg IgM/kg bodyweight | 3 |
| Day 4 | 42 mg IgM/kg bodyweight | 4 |
| Day 5 | 42 mg IgM/kg bodyweight | 5 |

FIG. 1 shows the IgM increase after 5 consecutive administrations of 42 mg IgM/kg bodyweight as defined herein in a healthy subject showing reproducible dose-dependent plasma PK levels.

Initial Study Results

Figure 2:
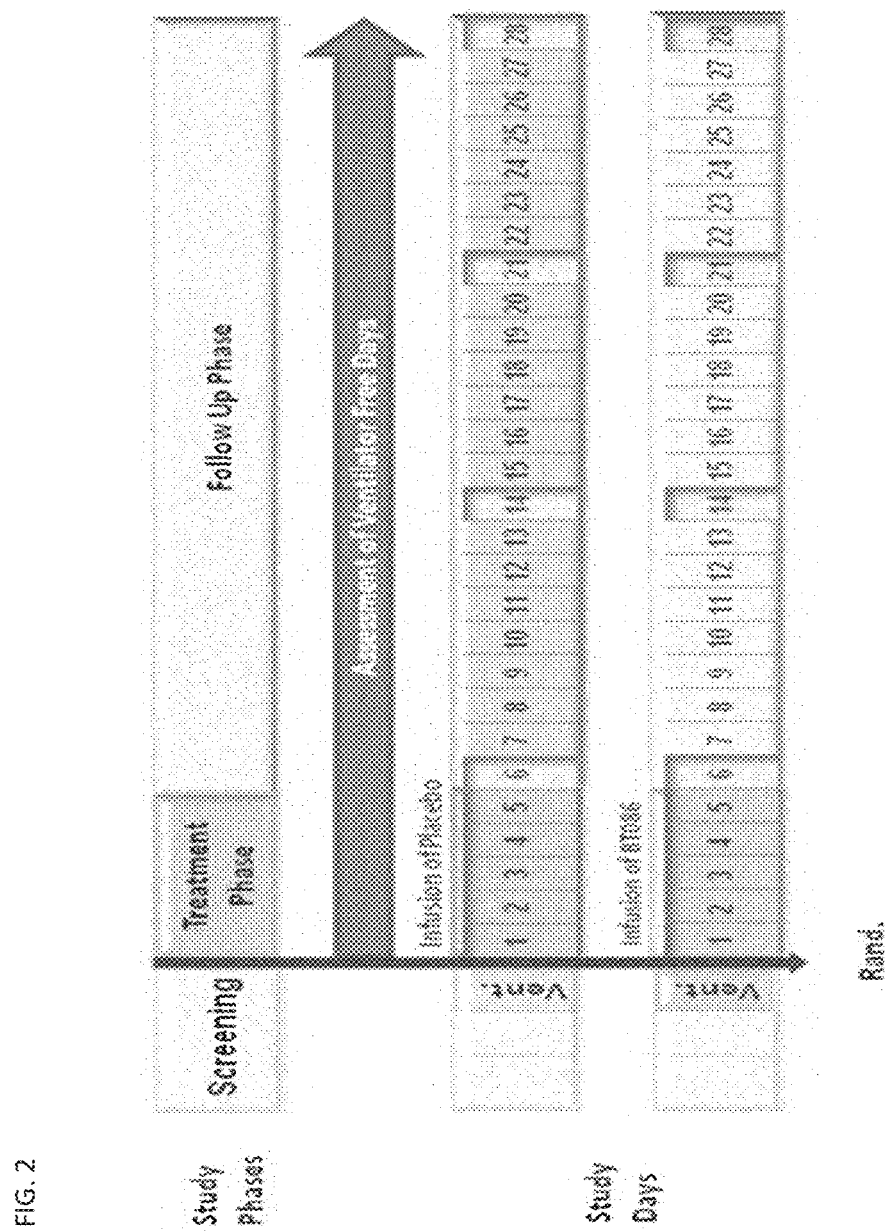
FIG. 2 shows the Phase II study design of study 982. Study 982 was divided into three study phases i.e., a screening-, a treatment- and a follow-up-phase. Patients suffering from severe community acquired pneumonia (sCAP) who required invasive mechanical ventilation were enrolled in this Phase II study. Eligible patients were randomized 1:1 to treatment with BT086 or placebo. Patients were treated with study medication once daily on five consecutive days (Day 1 until Day 5) and remained in the study up to Day 28 or hospital discharge whatever occurred earlier. An additional safety follow-up until Day 43 was performed only for patients recruited in the UK to meet local regulatory requirements. Primary endpoint was the increase of ventilator-free days (VFDs) determined in sCAP patients treated with adjunctive BT086 and the appropriate standard-of-care treatment as compared to patients treated with placebo and the appropriate standard of care. Abbreviations: Vent., start of ventilation; Rand., randomization

FIG. 2 outlines the study design. The primary endpoint was ventilator-free days (VFDs). One of the secondary endpoints was mortality level after administration of BT086 as a treatment adjunctive to standard of care.

VFDs are defined as the number of days between successful extubation (weaning) from mechanical ventilation and day 28 after enrollment of the patient into the study. The VFD is "0" if the patient dies before end of follow up (28 days), even after successful weaning. Therefore, VFDs combine mortality and duration of ventilation in survivors (Schoenfeld et al. 2002 Crit Care Med 30(8):1772-1777 (2002)).

Figure 3:
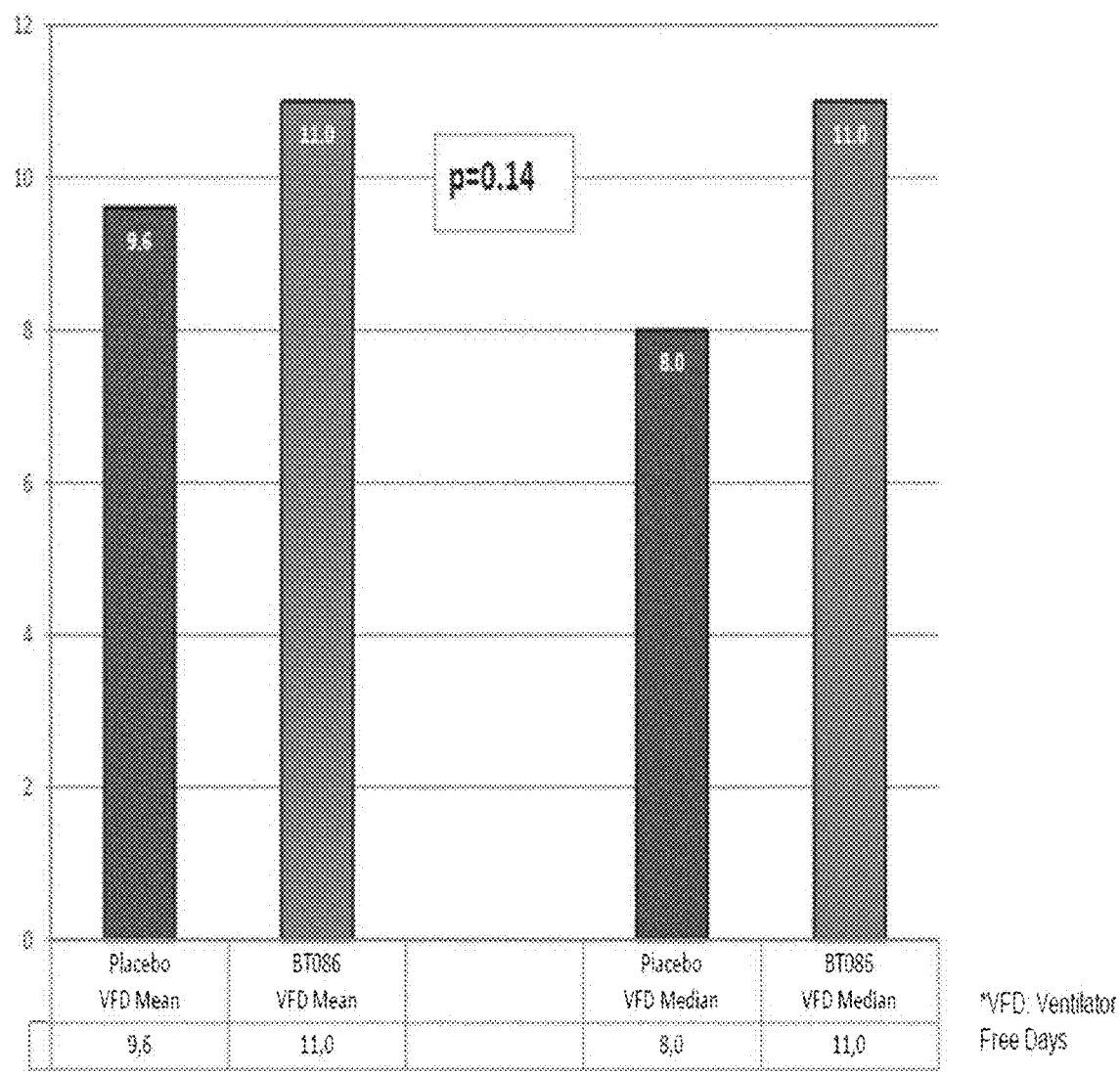
FIG. 3 shows the number of ventilator-free days (VFD) in sCAP patients treated with the IgM-enriched immunoglobulin preparation (BT086) as described herein as compared to VFD in patients treated with placebo. The p-value refers to the difference between the mean values.
Figure 4:
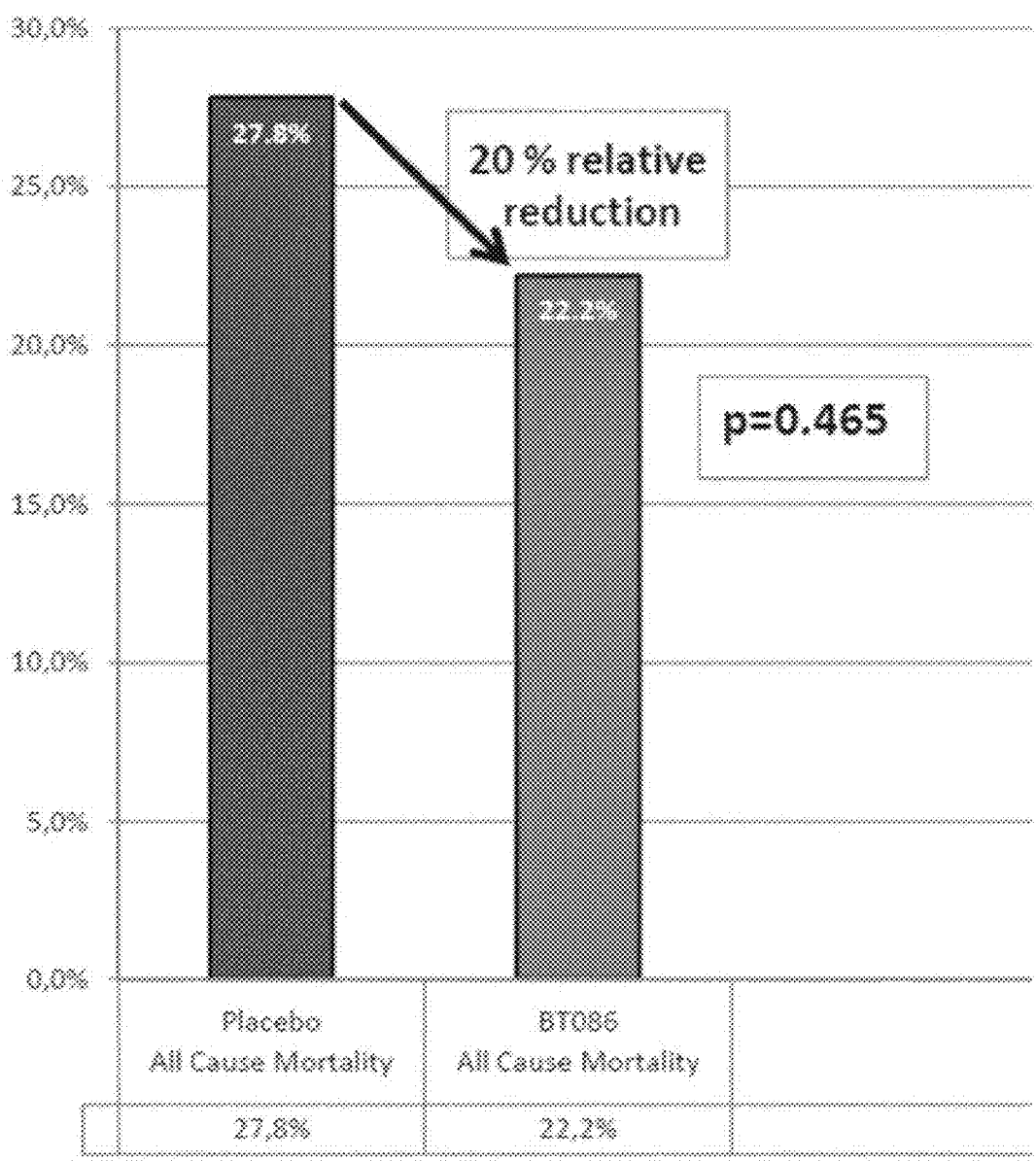
FIG. 4 shows the percentage mortality in sCAP patients treated with the IgM-enriched immunoglobulin preparation (BT086) as described herein as compared to percentage mortality patients treated with placebo. The p-value refers to the difference between the all-cause mortality values.

FIGS. 3 and 4 show the difference in respectively VFDs and 28—day mortality in patients treated with the immunoglobulin preparation as defined herein as an adjunctive treatment, and in patients treated with placebo as defined above as an adjunctive treatment. As can be seen from FIG. 3, an increase of 1.4 VFDs can be observed in the complete patient population inscribed in the study for the immunoglobulin preparation treated patients vs. placebo treated patients. In the study, a 5% absolute reduction of all-cause mortality was observed as compared to the placebo group, the relative reduction being higher. FIG. 3 shows a difference of about 20% relative reduction of all-cause mortality in patients treated with the immunoglobulin preparation as defined herein as an adjunctive treatment, versus patients treated with placebo as an adjunctive treatment. In addition, a 51% relative reduction of pneumonia caused mortality was observed.

Interestingly, in the course of the further analysis of the study, it was found that patients with certain levels of the inflammatory markers CRP and PCT or certain levels of immunoglobulins benefit more from treatment with the IgM-enriched immunoglobulin preparation than other patients. It has also been found in the further analysis of the study that male patients benefit more from treatment with the IgM-enriched immunoglobulin preparation than female patients. It has also been found in the analysis of the study that patients not older than 65 years benefit more from treatment with the IgM-enriched immunoglobulin preparation than older patients.

Example 3

Figure 7:
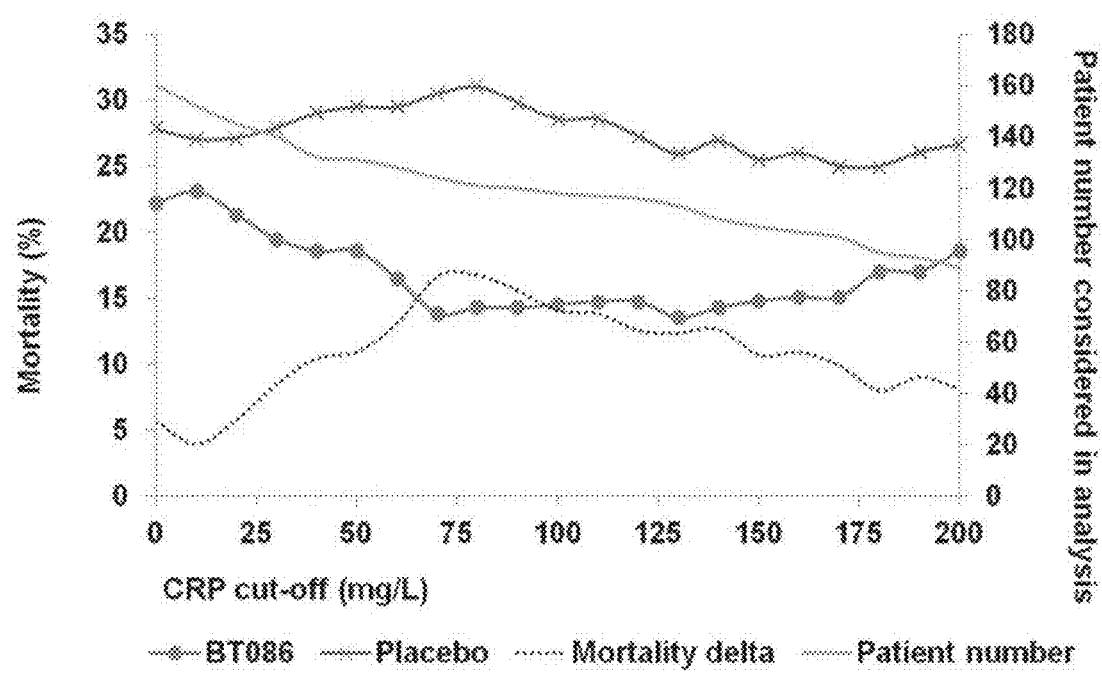
FIG. 7 shows mortality data for blood serum CRP cut-off levels plotted against the difference in mortality (mortality delta) between patients treated with the IgM-enriched immunoglobulin preparation as described herein (BT086) and patients treated with the placebo as described herein. Data are given for patients with CRP levels equal or above the respective cut-off level. The levels were measured pre-dose, within 24 hours before treatment, almost all within 12 hours before start of treatment. The figure shows a clear trend in mortality delta in patients having higher CRP serum levels. The mortality delta peaks at a cut-off level of about 70 mg/l (16.9% difference in absolute mortality). The minimal difference is observed at a cut-off level of 10 mg/l (4% difference in mortality). Patient numbers (solid line) refers to the number of patients in the study which show values equal to or above the respective cut-off level.
Figure 8:
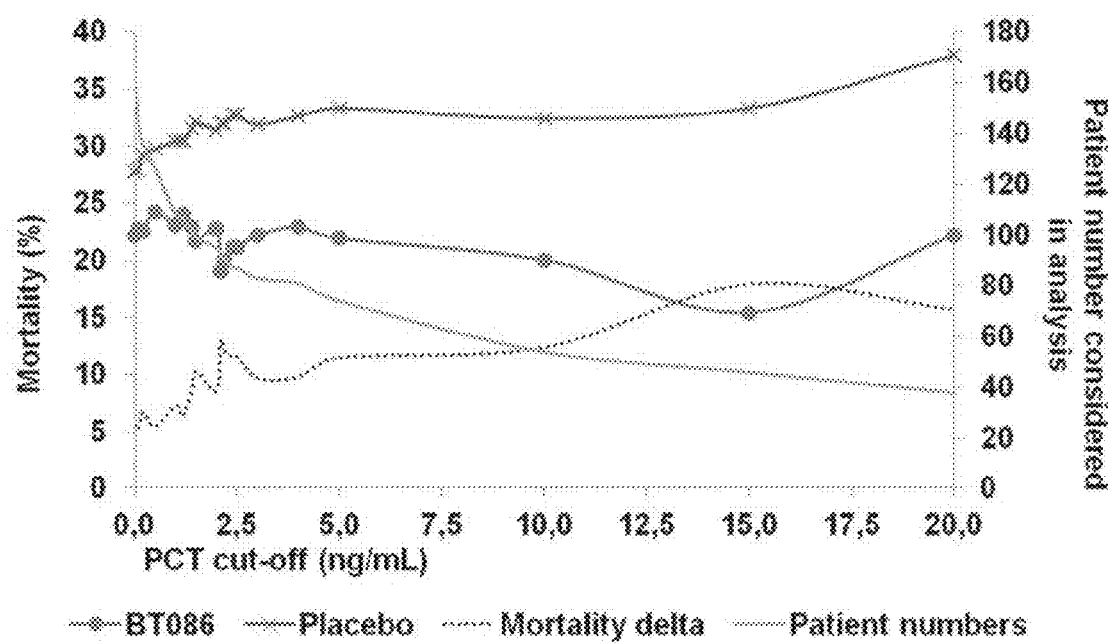
FIG. 8 shows mortality data for blood serum PCT cut-off levels plotted against the difference in mortality (mortality delta) between patients treated with the IgM-enriched immunoglobulin preparation as described herein (BT086) and patients treated with the placebo as described herein. Data are given for patients with PCT levels equal or above the respective cut-off level. The levels were measured pre-dose, within 24 hours before treatment, almost all within 12 hours before start of treatment. Blood serum PCT cut-off levels plotted against the difference in mortality (mortality delta) between Ig-treated and placebo patients. As with CRP, the figure shows a positive trend in mortality delta between immunoglobulin-treated versus placebo treated patients when higher PCT values are present in blood serum. At a cut-off value of 1.5 ng/ml PCT, the mortality delta is already above 10%. A difference in mortality of 13% is observed applying a cut-off of 2.1 ng/ml, a difference in absolute mortality of 17.9% is observed at a cut-off of 15 ng/ml. Patient numbers (solid line) refers to the number of patients in the study which show values equal or above the respective cut-off level (see right hand vertical axis)
Figure 9:
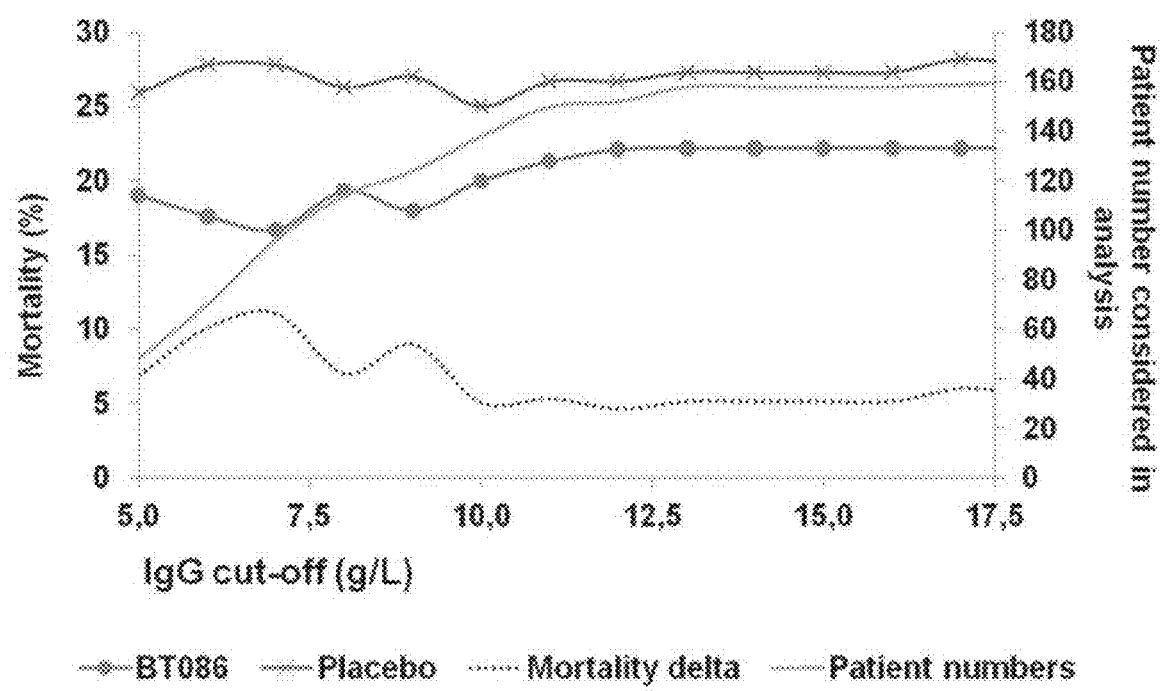
FIG. 9 shows mortality data for blood serum IgG cut-off levels against the difference in mortality (mortality delta, dotted line) between patients treated with the IgM-enriched immunoglobulin preparation as described herein (BT086) and patients treated with the placebo as described herein. Data are given for patients with IgG values equal to or below the respective cut-off level. The levels were measured pre-dose, within 24 hours before treatment, almost all within 12 hours before start of treatment. Blood serum IgG cut-off levels plotted against the difference in mortality (mortality delta) between Ig-treated and placebo patients. In patients with IgG levels of equal to or below about 10 g/l IgG, the mortality delta of immunoglobulin-treated versus placebo-treated starts increasing. A maximum of the mortality delta (11.1%) is observed for a cut-off level of about 7 g/l IgG. Patient numbers (solid line) refers to the number of patients in the study which show values equal or above the respective cut-off level.

CRP Levels Indicate the Presence of Different Responses in Subgroups Within the sCAP Population In example 2, the envisaged study end-point of increase of 2 VFDs of patients treated with the immunoglobulin preparation as defined herein as an adjunctive treatment, versus patients treated with placebo as an adjunctive treatment was not reached. Upon further analysis of the treatment results, it was found that patients responding better to treatment with BT086 had higher CRP levels at start of treatment. These data are shown in FIG. 7. The figure shows a clear trend in mortality delta in patients having higher pre-dose CRP serum levels. The mortality delta peaks at a cut-off level of about 70 mg/l (16.9% difference in absolute mortality). The minimal difference is observed at a cut-off level of 10 mg/l (4% difference in mortality). The range of cut-off values between about 50 to about 100 mg/l seems to be of particular interest, because the benefit of these patients is high, while a high fraction of patients benefits from the treatment. One should consider that a 16.9% difference in absolute mortality means three-fold reduction in mortality compared to the total patient collective, In another example, using a cut-off of 100 mg/l, a clear reduction of all-cause 28 day-mortality (50%) and a clear increase of mean VFDs (>2 days) was seen as shown in the table below VFDs and 28-day all-cause mortality for patients with a serum CRP cut-off value of 100 mg/l at day −1 or 1 of start of treatment.

| Treatment: | | Placebo | IgM preparation (BT086) |
|---|---|---|---|
| | Patients total: | 79 | 81 |
| CRP measurement missing | N | 3 | 1 |
| CRP > 100 mg/l | VFD (mean) | 9.2 | 11.8 |
| | VFD (median) | 5.5 | 12.0 |
| | 28-day | 16/56 | 9/63 |
| | Mortality | 28.6% | 14.3% |

For the analysis, the last CRP value before start of treatment with BT086 (which was within 1 to 12 hours after start of invasive mechanical ventilation) was considered. This value was always within 24 hours before BT086 treatment start, in almost all cases within 12 hours before BT086 treatment start. The same applies to the other levels mentioned in the following examples (PCT, IgM, etc.)

Example 4

PCT Levels Indicate the Presence of Different Responses in Subgroups within the sCAP Population It was found that also another marker showed a striking potential to predict benefit of treatment with the IgM enriched immunoglobulin preparation. At a cut-off value of 1.5 ng/ml PCT, the mortality delta is already at 10.3%. A difference in mortality of 13% is observed applying a cut-off of 2.1 ng/ml, a difference in absolute mortality of 17.9% is observed at a cut-off of 15 ng/ml. However, with increasing cut-off levels, the number of patients treated becomes smaller.

As can be seen in the table below, the mean number of VFDs went up with more than 3 days and the 28 day-mortality incidence decreased with more than 10% in IgM group versus placebo group.

VFDs and 28 day all-cause mortality for patients with a serum PCT cut-off value of at least 2 ng/ml at day −1 or 1 of start of treatment

| Treatment: | | Placebo | IgM preparation (BT086) |
|---|---|---|---|
| | Patients total: | 79 | 81 |
| PCT measurement missing | N | 9 | 6 |

| VFDs and 28 day all-cause mortality for patients with a serum PCT cut-off value of at least 2 ng/ml at day −1 or 1 of start of treatment | | | |
|---|---|---|---|
| Treatment: | | Placebo | IgM preparation (BT086) |
| PCT > 2 ng/ml | VFD (mean) | 7.8 | 11.2 |
| | VFD (median) | 3.0 | 11.0 |
| | 28 day- | 16/51 | 10/43 |
| | Mortality | 31.4% | 23.3% |

Example 5

Figure 6:
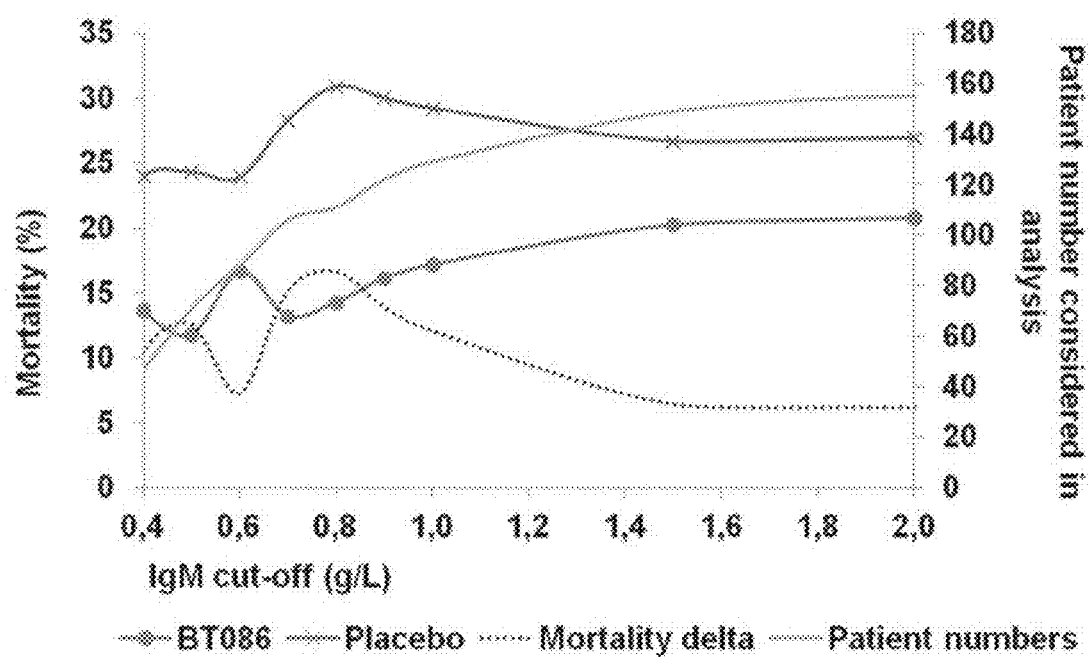
FIG. 6 shows mortality data for blood serum IgM cut-off levels above the limit of detection plotted against the difference in mortality (mortality delta, dotted line) between sCAP patients treated with the IgM-enriched immunoglobulin preparation as described herein (BT086) and patients treated with the placebo as described herein. Data are given for patients with IgM values equal to or below the respective cut-off level. The levels were measured pre-dose, within 24 hours before treatment, almost all within 12 hours before start of treatment. From the figure it becomes clear that the mortality delta increases if a cut-off below or equal to 1.5 g/l IgM is chosen. The maximum difference (16.6%) is observed for a cut-off of 0.8 g/l. A difference of 10.3% is observed at a cut-off of 0.4 g/l. Patient numbers (solid line) refers to the number of patients in the study which show values equal to or below the respective cut-off level. E.g. 47 patients has an IgM level of equal to or less than 0.4 g/l, whereas 111 patients had an IgM level of equal to or less than 0.8 g/l, and 129 patients had an IgM level of equal to or less than 1.0 g/l. It will be appreciated by the skilled person that higher patient numbers provide a better database for analysis and that one can choose appropriate cut-off levels allowing to treat a high number of patients while maintaining a good benefit of the treatment.

IgM Levels Indicate the Presence of Different Responses in Subgroups within the sCAP Population Further to examples 3 and 4, the patients serum level of IgM before start of treatment was also found to be a strong independent predictor of improved benefit of treatment (FIG. 6). From the data in FIG. 6 it can be seen that the mortality delta increases if a cut-off below or equal 1.5 g/l IgM is chosen. This maximum difference (16.6%) is observed for a cut-off of 0.8 g/l. A difference of 10.3% is observed at a cut-off of 0.4 g/l. Patient numbers (solid line) refers to the number of patients in the study which show values equal or below the respective cut-off level. E.g. 47 patients has an IgM level of equal or less than 0.4 g/l, whereas 111 patients had an IgM level of equal or less than 0.8 g/l, and 129 patients had an IgM level of equal or less than 1.0 g/l. It will be appreciated by the skilled person that higher patient numbers provide a better database for analysis and that one can choose appropriate cut-off levels allowing to treat a high number of patients while maintaining a good benefit of the treatment.

As can be seen in the table below, the mean number of VFDs went up with more than 3 days and the 28 day-mortality incidence decreased with more than 12% in the IgM preparation treated versus placebo treated patients.

| VFDs and all-cause 28 day-mortality for patients with a plasma IgM cut-off value of 0.5 g/l at day −1 or 1 of start of treatment | | | |
|---|---|---|---|
| Treatment: | | Placebo | IgM preparation (BT086) |
| | n | 37 | 34 |
| IgM <= 0.5 g/l | VFD (mean) | 9.8 | 13.0 |
| (low) | VFD (median) | 8.0 | 15.0 |
| | 28 day- | 9/37 | 4/34 |
| | Mortality | 24.3% | 11.8% |
| | n | 42 | 47 |
| IgM > 0.5 g/l | VFD (mean) | 9.5 | 9.6 |
| (normal | VFD (median) | 6.0 | 8.0 |
| or high) | 28 day- | 13/42 | 14/47 |
| | Mortality | 30.9% | 29.8% |

Example 6

IgA Levels Indicate the Presence of Different Responses in Subgroups Within the sCAP Population In addition to the previous examples, the mortality data for blood serum IgA cut-off levels were plotted against the difference in mortality (mortality delta, dotted line) between patients treated with the IgM-enriched immunoglobulin preparation as described herein (BT086) and patients treated with the placebo as described herein (cf. FIG. 10).

Data are given for patients with IgA values equal or below the respective cut-off level. The levels were measured pre-dose, within 24 hours before treatment, almost all within 12 hours before start of treatment.

As can be derived from the figure, the mortality delta of immunoglobulin-treated versus placebo-treated starts increasing in patients with IgA levels of equal to or below about 4 g/l IgA. At a cut-off level of about 3 g/l IgA, a difference in mortality of 9.5% is observed, which further increases to more than 10% for lower cut-off values. Patient numbers (solid line) refers to the number of patients in the study which show values equal or above the respective cut-off level.

Example 7

CRP and IgM Levels Indicate the Presence of Different Responses in Subgroups Within the sCAP Population In a further addition to the previous examples, further details for cut-off levels CRP equal or greater than 70 mg/l, for IgM equal or lower than 0.8 g/l, and for the group of patients fulfilling both criteria, including baseline data, are shown in the following table:

| | | Placebo | BT086 |
|---|---|---|---|
| Baseline values | Patients total | 79 | 81 |
| | CRP missing (n) | 3 | 1 |
| CRP ≥ 70 mg/l | n | 59 | 65 |
| | Mortality (n) | 18 | 9 |
| | Mortality (%) | 30.5% | 13.9% |
| | Age (mean) | 63.3 | 62.5 |
| | Apache II (mean) | 25.2 | 22.3 |
| IgM ≤ 0.8 g/l | n | 55 | 56 |
| | Mortality (n) | 17 | 8 |
| | Mortality (%) | 30.9% | 14.3% |
| | Age (mean) | 66.8 | 62.8 |
| | Apache II (mean) | 25.9 | 22.3 |
| CRP ≥ 70 mg/l & IgM ≤ 0.8 g/l | n | 41 | 51 |
| | Mortality (n) | 15 | 6 |
| | Mortality (%) | 36.6% | 11.8% |
| | Age (mean) | 66.1 | 61.6 |
| | Apache II (mean) | 25.0 | 21.7 |

From the baseline data, it can be seen that the demographics of placebo and treatment groups are comparable, but the difference in mortality in the stratified groups is remarkable. Descriptive p-values from a Fisher's Exact Test with a significance level of 0.05 have been calculated for the stratified groups. According to this calculation, the differences in mortality are significant (p=0.030 for CRP equal or greater than 70 mg/l, p=0.042 for IgM equal or lower than 0.8 g/l, and p=0.006 for the group of patients fulfilling both criteria).

APACHE II ("Acute Physiology and Chronic Health Evaluation II") is a severity-of-disease classification system (Knaus W A, Draper E A, Wagner D P, Zimmerman J E (1985). "APACHE II: a severity of disease classification system". Critical Care Medicine 13 (10): 818-29). APACHE II was designed to measure the severity of disease for adult patients admitted to intensive care units.

The invention claimed is:

1. A method of treating severe Community Acquired Pneumonia (sCAP) in a patient comprising administering to the patient a therapeutically effective amount of a human plasma-derived IgM-enriched immunoglobulin preparation, said immunoglobulin preparation not having been treated with beta-propiolactone said patient has a serum C-Reactive Protein (CRP) level of at least 70 mg/L and/or a serum procalcitonin (PCT) level of at least 2.0 ng/ml.

2. The method of claim 1, wherein the immunoglobulin preparation comprises from 10 to 40% by weight IgM of the total immunoglobulin content.

3. The method of claim 2, wherein the immunoglobulin preparation comprises from 18 to 28% by weight IgM of the total immunoglobulin content.

4. The method of claim 1, further comprising administering vasopressor therapy or invasive mechanical ventilation; wherein said serum procalcitonin (PCT) and/or C-Reactive Protein (CRP) level is present at the time of severe Community Acquired Pneumonia (sCAP) diagnosis and is present at least once within 24 hours before to 24 hours after the start of vasopressor therapy and/or the start of invasive mechanical ventilation.

5. The method of claim 1, wherein the plasma-derived IgM-enriched immunoglobulin preparation is adjunctive to antibiotic therapy.

6. The method of claim 1, wherein the immunoglobulin preparation comprises from 15 to 27% by weight IgA of the total immunoglobulin content.

7. The method of claim 1, wherein the immunoglobulin preparation comprises from 48 to 66% by weight IgG of the total immunoglobulin content.

8. The method of claim 1, wherein the immunoglobulin preparation has a total immunoglobulin content of at least 90% by weight of the total protein content.

9. The method of claim 1, wherein the immunoglobulin preparation is in the form of a solution for intravenous administration comprising between 40 and 100 grams immunoglobulin per liter solution.

10. The method of claim 1, further comprising administering vasopressor therapy or invasive mechanical ventilation; wherein the immunoglobulin preparation is administered in 3 to 10 daily doses over 21 days, wherein a first daily dose is administered within 24 hours after vasopressor therapy and/or invasive mechanical ventilation.

11. The method of claim 1, further comprising administering vasopressor therapy or invasive mechanical ventilation; wherein the immunoglobulin preparation is administered according to the following treatment regimen: a first daily dose to be administered within 24 hours after the start of vasopressor therapy and/or invasive mechanical ventilation, followed by daily infusions for 3 to 10 consecutive days.

12. The method of claim 1, wherein a daily dosage of the immunoglobulin preparation of between 30 and 80 mg IgM/kg bodyweight is administered.

13. The method of claim 1, wherein the immunoglobulin preparation administered to the patient is derived from at least 500 plasma donors.

14. The method of claim 1, wherein an initial daily dose between 50 and 80 mg IgM/kg bodyweight is administered.

15. The method of claim 14, wherein the infusion rate is equal or less than 6 mg IgM/min.

16. The method of claim 1, wherein the patient has a serum IgM level of equal to or lower than 1.5 g/L, and/or a serum IgG level of equal to or lower than 10 g/L, and/or a serum IgA level of equal to or lower than 4.0 g/L.

17. The method of claim 16, wherein the serum IgM level is equal to or lower than 1.0 g/L and/or wherein the IgG level is equal to or lower than 9 g/L.

18. The method of claim 16, further comprising administering vasopressor therapy or invasive mechanical ventilation; wherein said serum IgM, IgG, or IgA level is present at least once within 24 hours before to 24 hours after the start of vasopressor therapy or invasive mechanical ventilation.

19. The method of claim 16, further comprising administering vasopressor therapy or invasive mechanical ventilation; wherein said serum IgM, IgG, or IgA level is present at the time of severe Community Acquired Pneumonia (sCAP) diagnosis.

20. The method of claim 19 wherein said serum IgM, IgG, or IgA level is present at least once within 24 hours before to 24 hours after the start of vasopressor therapy or invasive mechanical ventilation.

21. A method of treating severe Community Acquired Pneumonia (sCAP) in a patient, comprising the steps of:
    (a) detecting the serum C-Reactive Protein (CRP) level, and/or serum procalcitonin (PCT) level, in a blood sample of the patient, wherein a serum CRP level of at least 70 mg/L and/or a serum PCT level of at least 2.0 ng/ml indicates the patient is a patient who may benefit from adjunctive treatment with a human plasma-derived IgM-enriched immunoglobulin preparation; and
    (b) administering to the patient identified in step (a) a therapeutically effective amount of the human plasma-derived IgM-enriched immunoglobulin preparation, the human plasma-derived IgM-enriched immunoglobulin preparation not having been treated with beta-propiolactone.

22. The method of claim 21, comprising the steps of determining the serum IgM level and/or a serum IgG level in the blood sample of the patient, wherein a serum IgM level of equal to or lower than 1.5 g/L, and/or a serum IgG level of equal to or lower than 10 g/L, and/or a serum IgA level of equal to or lower than 4.0 g/L is indicative that the patient may benefit from the treatment.

23. The method of claim 22, wherein the serum IgM level is equal to or lower than 1.0 g/L and/or wherein the IgG level is equal to or lower than 9 g/L.

* * * * *